(12) United States Patent
Holmback et al.

(10) Patent No.: US 8,697,403 B2
(45) Date of Patent: Apr. 15, 2014

(54) PROCESS AND MICROORGANISMS FOR PRODUCTION OF LIPIDS FROM LIGNOCELLULOSIC WASTES OR RESIDUES

(75) Inventors: Maria Holmback, Piikkio (FI); Miina Lehesto, Piispanristi (FI); Perttu Koskinen, Helsinki (FI); Johan-Fredrik Selin, Helsinki (FI)

(73) Assignee: Neste Oil Oyj, Espoo (FI)

( * ) Notice: Subject to any disclaimer, the term of this patent is extended or adjusted under 35 U.S.C. 154(b) by 34 days.

(21) Appl. No.: 13/114,756

(22) Filed: May 24, 2011

(65) Prior Publication Data

US 2011/0294173 A1 Dec. 1, 2011

Related U.S. Application Data

(60) Provisional application No. 61/347,913, filed on May 25, 2010.

(30) Foreign Application Priority Data

May 25, 2010 (EP) .................................... 10163732

(51) Int. Cl.
*C12P 7/64* (2006.01)
*C12N 9/10* (2006.01)
*C12N 15/00* (2006.01)
*C12N 1/20* (2006.01)
*C07H 21/04* (2006.01)

(52) U.S. Cl.
USPC ... 435/134; 435/193; 435/320.1; 435/252.35; 435/253.5; 536/23.2

(58) Field of Classification Search
None
See application file for complete search history.

(56) References Cited

U.S. PATENT DOCUMENTS

| | | | |
|---|---|---|---|
| 6,043,200 | A | 3/2000 | Carroll et al. |
| 7,691,792 | B1 | 4/2010 | Fisher et al. |
| 2009/0064567 | A1 | 3/2009 | Lippmeier et al. |
| 2009/0148918 | A1 | 6/2009 | Trimbur et al. |
| 2010/0021711 | A1 | 2/2010 | Lee et al. |

FOREIGN PATENT DOCUMENTS

| | | |
|---|---|---|
| EP | 1396531 | 3/2004 |
| EP | 1398364 | 3/2004 |
| EP | 1741767 | 1/2007 |
| EP | 1741768 | 1/2007 |
| WO | 2004053108 | 6/2004 |
| WO | 2008086466 | 7/2008 |
| WO | 2009009391 | 1/2009 |
| WO | 2009011480 | 1/2009 |
| WO | 2009034217 | 3/2009 |
| WO | 2009046375 | 4/2009 |
| WO | 2009063138 | 5/2009 |
| WO | 2009118438 | 10/2009 |
| WO | 2010021711 | 4/2010 |
| WO | 2010042819 | 4/2010 |

OTHER PUBLICATIONS

Alvarez et al., "Triacylglycerols in prokaryotic microorganisms", Appl. Microbiol. Biotechnol., 2002, 60:367-376.
Arabolaza et al., "Multiple pathways for triacylglycerol biosynthesis in *Streptomyces coelicolor*", Applied and Environmental Microbiology, May 2008, 74(9):2573-2582.
Behal et al., "Regulation of biosynthesis of secondary metabolites", Folia Microbiol, 1969, 14:211-214.
Bertrand et al., "Expression of the xylanase gene of *Streptomyces lividans* and production of the enzyme on natural substrates", Biotechnology and Bioengineering, 1989, 33:791-794.
Campbell, "Biodiesel: Algae as a renewable source for liquid fuel", Guelph Engineering Journal, 2008, 1 (2-7):1916-1107.
Cote et al., "Cloning, purification and characterization of two lipases from *Streptomyces coelicolor* A3(2)", Enzyme and Microbial Technology, 2008, 42:381-388.
Gesheva et al., "Fatty acid composition of *Streptomyces hygroscopicus* strains producing antibiotics", Letters in Applied Microbiology, 1997, 24:109-112.
Kaddor et al., "Analysis of neutral lipid biosynthesis in *Streptomyces avermitilis* MA-4680 and characterization of an acyltransferase involved herein", Applied Microbial and Cell Physiology, 2009, 84:143-155.
Kieser et al., "Practical *Streptomyces* Genetics", Applied Microbiology and Biotechnology, Aug. 2009, 84 (1):143-155.
Lee et al., "Esterolytic and lipolytic activites of *Lactobacillus casei*-subsp-Casei LLG", Journal of Food Science, 1990, 55(1):119-122.
Li et al., "Alteration of the fatty acid profile of *Streptomyces coelicolor* by replacement of the initiation oenzyme 3-ketoacyl acyl carrier protein synthase III (FabH)", Journal of Bacteriology, Jun. 2005, 187(11):3795-3799.
Meng et al., "Biodiesel production from oleaginous microorganisms", Renewable Energy, 2009, 34:1-5.
Nagao et al., "Synthesis of 6-phosphatidyl-L-ascorbic acid by phospholipase D", Lipids, 1991, 26(5):390-394.

(Continued)

*Primary Examiner* — Iqbal H Chowdhury
(74) *Attorney, Agent, or Firm* — Andrus Intellectual Property Law, LLP

(57) ABSTRACT

Disclosed are processes for producing lipids for biofuel or lubricant and *Streptomyces* bacteria used in the processes. The processes include steps whereby bacterial cells of the germs *Streptomyces* are cultivated in a medium comprising organic waste(s) or residue(s) or mixtures thereof as carbon and/or nutrient source(s), wherein the organic waste(s) or residue(s) comprise lignocellulosic waste(s) or lignocellulosic residue(s), recovering lipids from the cells of the bacteria or from the cultivation medium, and using the recovered lipids or a fraction thereof as biofuel and/or lubricant, or as a starting material for biofuel and/or lubricant production.

13 Claims, 4 Drawing Sheets

(56) References Cited

OTHER PUBLICATIONS

Novak et al., "Nitrogen regulation of fatty acids and avermectins biosynthesis in *Streptomyces avermitilis*", FEMS Microbiology Letters, 1992, 93:57-62.
Olukoshi et al., "Importance of stored triacylglycerols in *Streptomyces*: possible carbon source for antibiotics", Microbiology, 1994, 140:931-943.
Packter et al., "Ultrastructural studies of neutral lipid localisation in *Streptomyces* ", Arch Microbiol, 1995, 164:420-427.
Ratledge et al., "Down-stream processing, extraction, and purification of single cell oils", Single Cell Oils, 2005, 202-219.
Ratledge et al., "Microbial and algal oils: Do they have a future for biodiesel or as commodity oils?", Lipid Technology, Jul. 2008, 20(7):155-160.
Revill et al., "β-Ketoacyl acyl carrier protein synthase III (FabH) is essential for fatty acid biosynthesis in *Streptomyces*", Journal of Bacteriology, Jun. 2001, 183(11):3526-3530.
Rice et al., "EMBOSS: The European molecular biology open software suite", Tends Genet, 2000, 16:276-277.
Smirnova et al., "Engineered fatty acid biosynthesis in *Streptomyces* by altered catalytic function of β-Ketoacyl-acyl carrier protein synthase III", Journal of Bacteriology, Apr. 2001, 183(7):2335-2342.
Soror et al., "A cold-active esterase of *Streptomyces coelicolor* A3(2): from genome sequence to enzyme activity", J Ind Microbiol Biotechnol, 2007, 34:525-531.
Strobel et al., "The production of myco-diesel hydrocarbons and their derivatives by the endophytic fungus *Gliocladium roseum* (NRRL 50072)", Microbiology, 2008, 154:3319-3328.
Suutari et al., "Changes in fatty acid branching and unsaturation of *Streptomyces griseus* and *Brevibacterium fermentans* as a response to growth temperature", Applied and Environmental Microbiology, Jul. 1992, 58 (7):2338-2340.
Waltermann et al., "Key enzymes for biosynthesis of neutral lipid storage compounds in prokaryotes: Properties, function and occurrence of wax ester synthases/acyl-CoA: diacylglycerol acyltransferases", Biochimie, 2007, 89:230-242.
Ylihonko et al., "A gene cluster involfed in nogalamycin biosynthesis from *Streptomyces nogalater*: sequence analysis and complementation of early-block mutations in the anthracycline pathway", Mol Gen Genet, 1996, 251:113-120.
International Search Report for PCT/FI2011/050474 dated Aug. 23, 2011.
Written Opinion for PCT/FI2011/050474 dated Aug. 23, 2011.
Search Report for EP10163732.0 dated Aug. 19, 2010.
Grafe et al., "Occurrence of squalene and dehydrosqualene in streptomycetes", J Basic Microbiol, 1985, 25 (8):503-507.
Coen, "The Polymerase Chain Reaction", Current Protocols in Molecular Biology, Chapter 15, 2001,15.0.1-15.0.3.

PROCESS AND MICROORGANISMS FOR PRODUCTION OF LIPIDS FROM LIGNOCELLULOSIC WASTES OR RESIDUES

CROSS-REFERENCE TO RELATED APPLICATIONS

The present application claims the benefit under 35 U.S.C. §119(e) to U.S. Provisional Application No. 61/347,913, the content of which is incorporated herein by reference in its entirety.

FIELD OF THE INVENTION

The present invention relates to a process for producing lipids for biofuel or lubricant applications and microbial strains useable in the process.

BACKGROUND OF THE INVENTION

The use of renewable biological material for the production of biofuels is generally motivated by decreasing climate change impacts, by securing the supply of fuels and by economic factors. However, the use of edible crops to create fuels instead of further refining them to food for increasing human population is more and more ethically short-lived. Therefore, biological sources that cannot be used for feeding of people or cattle and that can be manufactured in environmentally friendly manner, are of growing interest.

BCC Research estimates that the global market for liquid biofuels was worth $30.3 billion in 2008. This should increase to $42.8 billion in 2013, for a compound annual growth rate (CAGR) of 7.2 Another perspective to the market is the volume. In 2008 biofuel production capacity across the 21 countries considered in the study report of European Union totalled 10.9 billion liters of biodiesel, and 66.6 billion liters of bioethanol. Over 99% of this production is considered as so called 1st generation biofuel, including both sugar and starch based bioethanol, and oilseed and waste oil based biodiesel. Biodiesel can be made from oilseed crops, animal fats or from recycled greases. Since it is known that algae and sonic microorganisms are capable of producing and/or accumulating lipids, also their use as the source of oil for biodiesel has been suggested. These microorganism based oils are often called as single cell oils. Campbell 2008 and Strobel et al., 2008 have described optimization of the cultivation conditions of algae and fungi in different type of bioreactors to maximize the yields of lipids and fatty acids for refining of biofuels.

Alternative option to photosynthetic production of lipids is to utilize heterotrophic organisms which produce lipids from organic molecules (such as sugars) without need for light. Single cell oil production process using heterotrophic microorganisms comprises cultivating microorganisms in aerated bioreactors, allowing cells to accumulate lipids, harvesting lipid-rich cells and recovering oil from cells (Ratledge et al., 2005, Meng et al., 2009).

Single-cell oils have traditionally been used as special products e.g. in health foods, not as commodity chemicals. In these kinds of single cell oil production processes product volumes are relatively small and the product is expensive. Therefore, the cost structure of these processes allows the utilization of expensive feed raw materials and unit operations. Similar kind of production process has also been described for the production of lipids for biodiesel production (Ratledge and Cohen 2008; Meng et al. 2009). However, as the product is an inexpensive commodity chemical, the process costs should not be on the level of the process costs of special products. Further, the lipid yield by heterotrophic microorganisms is typically very low, less than 20% weight percent of the fed sugar (Ratledge and Cohen, 2008).

Less expensive raw materials for use in lipid production by heterotrophic microorganisms have been suggested in some recent patent publications. WO 2009/034217 A1 has described a fermentation method to make paraffins, fatty acids and alcohols by waste materials and microbes. WO 2009/046375 A2 suggests the conversion of polysaccharides derived from biomass into monosaccharides, or oligosaccharides and converting them into biofuels by using recombinant microorganisms comprising exogenous genes that allow the microorganism to grow on the polysaccharide as a sole source of carbon. US 2009/0064567 A1 discloses the production of biological oils by heterotrophic fermentation by growing microorganism of the kingdom *Stramenophile* by using cellulose-containing feedstock as a main source of carbon. WO2009/011480 A1 discloses the production of biological oils from depolymerised cellulosic material by microalgae and fungi. US 2009/0148918 A1 discloses a method of lipid manufacturing by culturing a microalgae on glycerol as a source of carbon. In addition WO 2009/009391 A2 discloses the production of fatty esters by first producing an alcohol composition and providing it into a fatty ester production host. WO 2009/063138 describes a method for treating organic material with water, acid or alkali and grinding. A precipitate and filtrate are separated and used for lipid production in a cultivation medium for a lipid producing microorganism.

Since the economy of the production of single cell oils for biofuels is of key importance, new cost-effective processes for lipid production for biofuel production are still of growing interest.

SUMMARY OF THE INVENTION

One object of the present invention is to provide a cost-effective process for producing lipids for biofuel or for lubricant applications.

Another object of the present invention is to provide new microorganisms which can be used in said process.

The invention described herein provides, in one aspect, a process for producing lipids, in particular for biofuel or for lubricant use. The invention is based on the finding that *Streptomyces* bacteria are able to produce effectively lipids on a medium comprising organic waste(s) and/or residue(s).

The process comprises cultivating bacterial cells of the genus *Streptomyces* in a medium comprising organic waste(s) or residue(s) or mixtures thereof as carbon and/or nutrient source(s). The process comprises the recovery of lipids from the cells of the bacteria or from the cultivation medium. The lipids or a fraction thereof are useful as biofuel and/or lubricant or as starting material for biofuel and/or lubricant production.

In various embodiments of the invention the cultivation medium can comprise organic waste(s) or residue(s) from industry, including agriculture, municipal waste or microbial residues.

Furthermore, the cultivation medium can comprise additional carbon source(s), such as glycerol or a fraction from sugar or starch industry.

In one embodiment of the invention the process can use not sterilized cultivation medium.

In another embodiment of the invention the process can use pasteurized cultivation medium.

In some embodiments of the invention the cultivation medium can comprise lipase inhibitors. Lipase inhibitors can be used to retard or hinder the hydrolysis of acylglycerols or degradation of lipids formed in the process.

In one embodiment of the invention the cultivation is carried out as a batch fermentation.

In another embodiment of the invention the cultivation is carried out as a fed-batch fermentation.

As disclosed herein the process produces lipids which comprise mainly TAGs (triacylglycerols). Typically the amount of TAGs in the spent cultivation medium is at least 1 g/liter of the medium.

Various *Streptomyces* species can be used in the invention. The species comprise, preferably the species may be selected from the group comprising, more preferably the species may be selected from the group of *Streptomyces roseosporus, Streptomyces griseus, Streptomyces albus, Streptomyces peucetius, Streptomyces aureofaciens Streptomyces lividans, Streptomyces coelicolor, Streptomyces hygroscopicus, Streptomyces avermitilis, Streptomyces milbemycenius* and *Streptomyces lydicus.*

*Streptomyces* strains comprise, preferably the strains may be selected from the group comprising, more preferably the strains may be selected from the group of strains *Streptomyces roseosporus* GAL4111, *Streptomyces roseosporus* G011, *Streptomyces griseus* GAL1005, *Streptomyces albus* GAL1001, *Streptomyces peucetius* D2, GAL4082, *Streptomyces peucetius* P55 GAL4081, *Streptomyces aureofaciens* GAL1004, *Streptomyces lividans* GAL1002, *Streptomyces coelicolor* GAL1003, *Streptomyces hygroscopicus* GAL4051, *Streptomyces avermitilis* GAL1006, *Streptomyces milbemycinius* GAL4211 and *Streptomyces lydicus* GAL1007.

Advantageous in the process of the present invention are *Streptomyces* species or strains that produce no or only low amounts of bioactive metabolites.

In a specific embodiment of the invention *Streptomyces* species or strains may be made deficient in producing bioactive metabolites. Examples of bioactive metabolites are for example antibiotic agents, such as lipopeptide antibiotics, for example daptomycin or milbemycin, or chemotherapeutic agents, such as daunomycin.

Strains producing low amounts of bioactive compounds or that are made deficient in producing bioactive compounds are for example strains comprising, preferably strains selected from the group comprising, more preferably strains may be selected from the group of *Streptomyces roseosporus* GAL4111, *Streptomyces roseosporus* G011, *Streptomyces griseus* GAL1005, *Streptomyces albus* GAL1001, *Streptomyces peucetius* P55 GAL4081 and *Streptomyces peucetius* D2 GAL4082 and *Streptomyces milbemycinius* GAL4211.

In one aspect the invention provides a *Streptomyces* culture, which comprises
(a) a population of bacteria of the genus *Streptomyces*; and (b) a cultivation medium comprising organic waste(s) or residue(s) or mixtures thereof as carbon and/or nutrient source(s).

In another aspect of the invention, the present invention provides new genetically modified *Streptomyces* hosts capable of effective lipid production.

In one embodiment of the invention *Streptomyces* host cells may be genetically modified to express at least one gene of the lipid biosynthesis pathway. In particular, the gene may be a gene encoding diacylglycerol acyltransferase (DGAT) and/or a gene encoding 3-ketoacyl-acyl carrier protein synthase III (FabH).

In one embodiment of the invention *Streptomyces* host cells may be genetically modified to express one or more of genes comprising, preferably selected from the group comprising, more preferably they may be selected from the group of (a) sco0958 (SEQ ID NO:1) and/or sco5888 (SEC) ID NO:2);
(b) the closest homologue of said genes in a *Streptomyces* species;
(c) a nucleotide sequence which hybridizes to at least one of said genes or said homologues under stringent conditions;
(d) a nucleotide sequence causing the same or an equivalent function as gene products ID 101096381 or ID 101101330 have; and/or
(e) a nucleotide sequence encoding an amino add sequence showing at least 60% identity to SEQ ID NO: 3 or SEQ ID NO:4.

In particular, suitable genetically modified strains are strains comprising, preferably selected from the group comprising, more preferably strains selected from the group of G009, G010, G012, G013, G014, G015, G016, G017 and G019.

In one specific embodiment of the present invention provides new *Streptomyces* strains selected from the group of G009, G010, G013, and G017.

In one further aspect the present invention provides use of any of the host cells, cultures or strains of *Streptomyces* for producing lipids and using the lipids as biofuel and/or lubricant or as a starting material for biofuel and/or lubricant production.

In addition, in one aspect the invention provides products obtained by using the process according to this disclosure.

Considerable advantages are obtained by means of the present invention. By means of the process and microorganisms presented here, it is possible to produce effectively lipids for biofuel and/or lubricant, or as a starting material for biofuel and/or lubricant production. The advantages of the present invention can be summarized as follows:

In the present invention it has surprisingly been found that *streptomycetes* can produce high amounts of lipids when cultivated on a medium comprising organic waste(s) and/or residue(s). The use of organic waste(s) and/or residue(s) as a carbon and/or nutrient source(s) reduces the costs of the cultivation medium, in particular because waste(s) and/or residue(s) are in-expensive and need no or only little pretreatment before use. The components of waste or residue materials need not to be necessarily separated, hydrolyzed (depolymerized), purified and/or sterilized before they are added to the cultivation medium.

The yield of lipids produced by *Streptomyces* in the process can be further increased by using lipase inhibitors in the cultivation medium. Lipase inhibitors are able to retard or hinder the hydrolysis of acylglycerols or degradation of lipids formed in the process.

The process as described here produces lipids which comprise mainly TAGS (triacylglycerols). The preferred compounds suitable for chemical processing for biofuel production are TAGs.

The efficiency of *Streptomyces* species or strains to produce lipids can be further improved by making the species or strains deficient in producing bioactive metabolites, such as antibiotic agents. The modified host strain has more capacity to produce lipids, when it is not producing bioactive metabolites.

The efficiency of lipid production can be further increased by producing new genetically modified *Streptomyces* hosts which may be genetically modified to express at least one gene of the lipid biosynthesis pathway.

In the following, the invention will be examined more closely with the aid of a detailed description and with reference to some working examples.

DETAILED DESCRIPTION OF THE INVENTION

Figure 1:
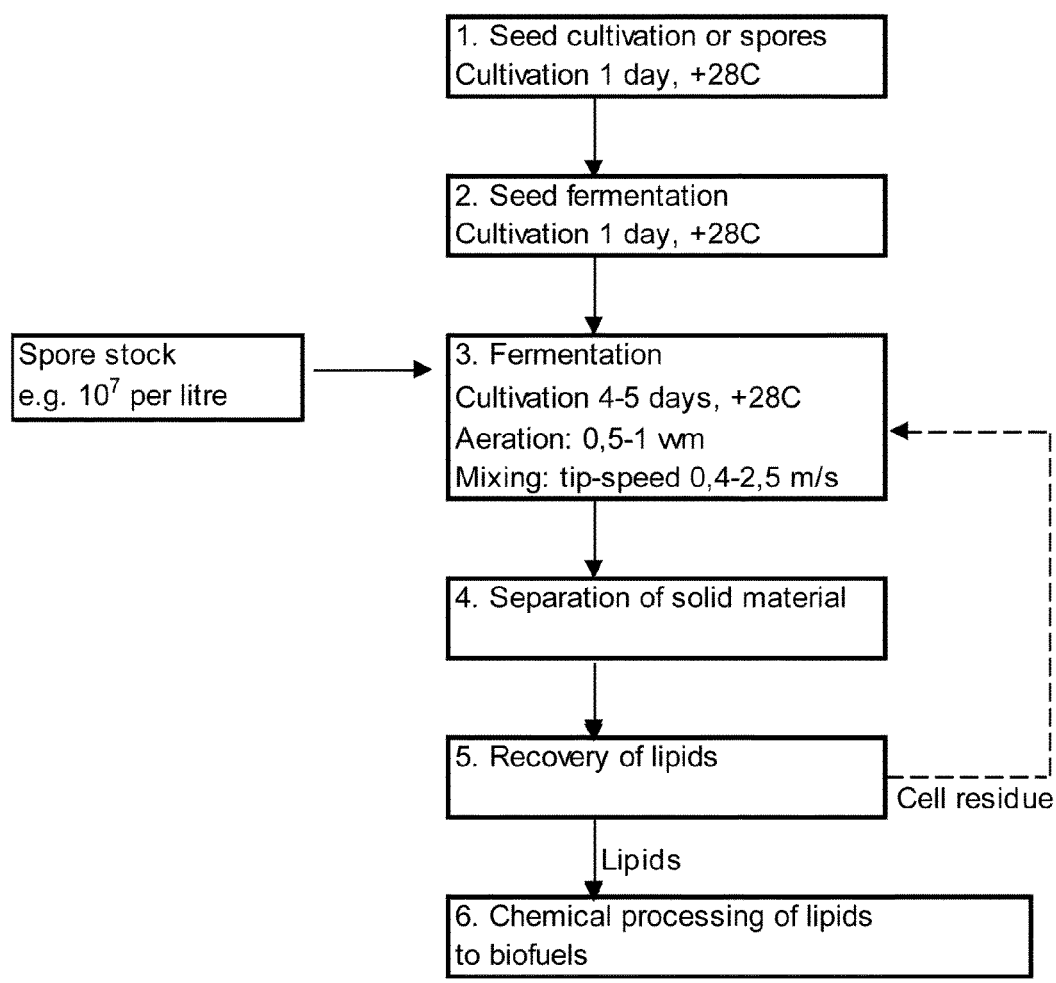
FIG. 1 presents the process scheme.
Figure 2:
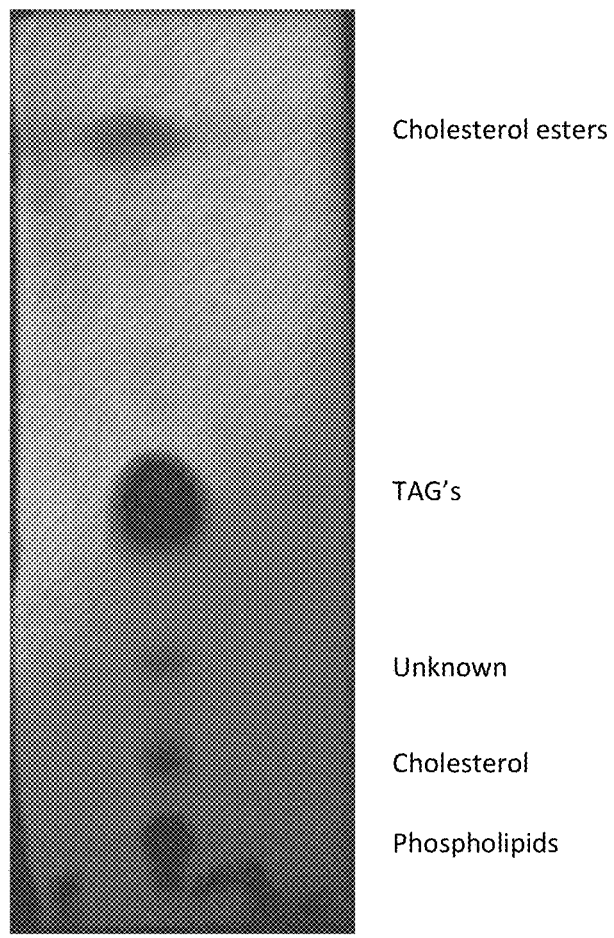
FIG. 2 depicts the TLC (Thin Layer Chromatography) profile of the strain G009.

"Biofuel" refers to solid, liquid or gaseous fuel mainly derived from biomass or biowaste and is different from fossil fuels, which are derived from the organic remains of prehistoric microorganisms, plants and animals.

According to EU directive 2003/30/EU "biodiesel" refers to a methyl-ester produced from vegetable oil or animal oil, of diesel quality to be used as biofuel. More broadly, biodiesel refers to long-chain alkyl esters, such as methyl, ethyl or propylesters, from vegetable oil or animal oil of diesel quality. Biodiesel can also be produced from microorganism lipids, whereby microorganism lipid can originate from a bacterium, a fungus (a yeast or a mold), an algae or another microorganism.

"Renewable diesel" refers to a fuel which is produced by a hydrogen treatment of lipids of an animal, vegetable or microorganism origin, or their mixtures, whereby microorganism lipid can originate from a bacterium, a fungus (a yeast or a mold), an algae or another microorganism. Renewable diesel can be produced also from waxes derived from biomass by gasification and Fischer-Tropsch synthesis. Optionally, in addition to hydrogen treatment, isomerization or other processing steps can be performed. Renewable diesel process can also be used to produce jet fuel and/or gasoline. The production of renewable diesel has been described in patent publications EP 1396531, EP1398364, EP 1741767 and EP1741768.

Biodiesel or renewable diesel may be blended with mineral oil based diesel. Suitable additives, such as preservatives and antioxidants may be added to the fuel product.

"Lubricant" refers to a substance, such as grease, lipid or oil, that reduces friction when applied as a surface coating to moving parts. Two other main functions of a lubricant are heat removal and to dissolve impurities. Applications of lubricants include, but are not limited to uses in internal combustion engines as engine oils, additives in fuels, in oil-driven devices such as pumps and hydraulic equipment, or in different types of bearings. Typically lubricants contain 75-100% base oil and the rest is additives. Suitable additives are for example detergents, storage stabilizers, antioxidants, corrosion inhibitors, dehazers, demuisifiers, antifoaming agents, cosolvents, and lubricity additives (see for example U.S. Pat. No. 7,691, 792). Base oil for lubricant can originate from mineral oil, vegetable oil, animal oil or from a bacterium, fungi (a yeast or a mold), an algae or another microorganism. Base oil can also originate from waxes derived from biomass by gasification and Fischer-Tropsch synthesis. Viscosity index is used to characterise base oil. Typically high viscosity index is preferred.

The term "lipid" refers to a fatty substance, whose molecule generally contains, as a part, an aliphatic hydrocarbon chain, which dissolves in nonpolar organic solvents but is poorly soluble in water. Lipids are an essential group of large molecules in living cells. Lipids are, for example, fats, oils, waxes, wax esters, sterols, terpenoids, isoprenoids, carotenoids, polyhydroxyalkanoates, nucleic acids, fatty acids, fatty alcohols, fatty acid esters, phospholipids, glycolipids, sphingolipids and acylglycerols.

The term "acyglycerol" refers to an ester of glycerol and fatty acids. Acylglycerols occur naturally as fats and fatty oils. Examples of acylglycerols include triacylglycerols (TAGs, triglycerides), diacylglycerols (diglycerides) and monoacylglycerols (monoglycerides).

The present invention relates to methods for efficient production of lipids by *streptomycetes* using cultivation media comprising organic waste(s) or residue(s) or mixtures thereof as a source of carbon and/or nutrient. In addition the cultivation media may comprise other components, such as mineral salts typically used in cultivating said microorganisms. The cultivation is carried out under conditions suitable for lipid production. The cultivation is typically carried out in a fermentor by using agitation and aeration.

In some embodiments of the invention organic waste(s) or residue(s) may be used as the sole or main carbon and/or nutrient source, or in some embodiments as (a) supplement(s). The waste or residue may comprise one or more different waste(s) or residue(s) or mixtures thereof.

If a waste or residue is the "main source of carbon and/or nutrient" in the medium, it means that on the basis of weight, the amount of waste is higher in the medium than the amount of pure ingredients (i.e. sugar) in the medium.

If a waste or residue fraction is used "as a supplement" it means that on the basis of weight, the amount of waste or residue fraction is lower in the medium than the amount of pure ingredients (i.e. sugar) in the medium.

In the present invention it has surprisingly been found that *Streptomyces* bacteria accumulate high amounts lipids and in particular of the triacylglycerols (TAGs) when cultivated on waste and/or residue materials.

Bacteria of the genus *Streptomyces* are well known in pharmaceutical industry. It is known that *streptomycetes* produce small molecules, useful enzymes and a variety of other metabolites by primary and secondary metabolism. Typically, aerobic fermentation processes are suitable to a variety of *Streptomyces* species since the methodology has been developed in many circumstances using these bacteria as model organisms. In the prior art processes *streptomycetes* are typically cultivated in complex media to enhance the accumulation of industrially useful metabolites, such as antibiotics. The costs of these fermentation processes are heavily influenced by material and purification costs. Sterilization needed to maintain the fermentation free of contaminants is extremely energy-consuming and the sterilization costs are high. Also when producing bulk antibiotics the energy needed for sterilization of the medium forms the major cost category in the process, although they are manufactured in large and simple fermentation tanks.

In the present invention it has surprisingly been found that *streptomycetes* can produce high amounts of lipids when cultivated on waste and residue materials. It is remarkable that the components of waste or residue materials need not to be necessarily separated, hydrolyzed (depolymerized), purified and/or sterilized before they are added to the cultivation media. Hence, in some embodiments waste material can be added to cultivation medium without any separation, hydrolysis (mechanical, chemical, or enzymatic), purification or sterilization. E.g. lignocellulosic materials can be used in cultivation and lipid production without hydrolysis (depolymerization) of polysaccharides. In other embodiments it can be added in crude form, i.e. comprising some preliminary purification, but being not purified to separate components. Furthermore, waste or residue can be added as such, or depending on the structure of the material, it can be added in grounded or mashed form to the cultivation medium. Wastes and/or residues can also be utilized in partly or completely purified, separated and hydrolyzed (depolymerized) form for lipid production by *Streptomyces*.

In the present disclosure "organic waste or residue" refers in particular to waste material, of which the components are not, or at least not completely, separated, hydrolysed (depolymerised) and/or purified. The use of waste or residue material without separation, hydrolysation (depolymerization) and/or purification of the components makes the process of the present invention more cost-effective compared to the use of pure ingredients. Nevertheless, in some embodiments of the invention pure ingredients may be used in cultivation media as carbon sources in addition to the waste material(s).

"Non-sterile organic waste or residue or cultivation medium comprising organic waste or residue" refers in particular to waste or residue material or medium, which is not sterilized. In some embodiments, the waste material or medium may be pasteurized.

By sterilization it is typically meant that the waste or residue material or medium comprising the waste or residue material is treated with high temperature, usually at 121° C., or higher, for at least 15 minutes, or for at least 20 minutes.

"Pasteurization" refers to the heating of a waste or residue material or medium comprising waste or residue material at 60° C.-75° C. for 2-30 minutes. As described herein even with high content waste or residue fractions up to 200 g/l, no living cells or spores were detected at ISA (Tryptone Soy Agar). In cultivations where pasteurized media instead of sterilized media were used, no differences were found in the growth of *streptomycetes*. The cultivation medium can comprise organic waste(s) or residue(s) or their combination with pure nutrients.

In some embodiments of the present invention a cultivation medium comprising organic waste or residue can be used as such, in some embodiments without sterilization by any method, or without pasteurization. "Non-sterile" means in those embodiments that cultivation medium with waste or residue material is not sterilized by any method.

In the present disclosure the waste or residue material or medium comprising the waste or residue material is not sterilized, in particular it is not sterilized with high temperature, such as at 121° C., or higher, or it is pasteurized.

In the present disclosure "organic waste or residue" refer in particular to waste or residue from industry including agriculture, municipal waste or microbial residue. Such waste or residue is typically (i) not used as food for people or animals and (ii) is formed in large quantities (typically in thousands or in millions of tonnes per annum globally). A large group of organic wastes from industry fulfils these criteria. "Organic waste or residue" refers to any waste or residue material or fraction that is biologically degradable.

Industrial waste or residue can comprise offal residue, organic waste or residue from food or feed production, e.g. from bakery, brewery, e.g. mash, malt extract, slaughter house, e.g. offal residue, meat or fish debris, sugar industry e.g. sugar beet pulp, or wood derived cellulosic or lignocellulosic materials or residues, or agricultural residues, such as grain residues, for example bran, chaff, straw, stalks, sugar cane bagasse, or other plants such as cellulosic crops, switchgrass, reed canary grass, *Miscanthus*, fiber *sorghum*, fiber cane, or plant residues, such as corn steep liquor (CSL), or glycerol for example from biodiesel production.

Municipal waste can comprise municipal sludge, waste paper, biowaste of institutional kitchen or households, organic waste of garden or organic waste of food production.

Microbial waste can comprise microbial cells or cell debris (for example *lactobacilli, streptomycetes*) for example from industrial processes based on the use of microorganisms, or algae debris (e.g. *Phaeodactylum, Chlorella, Dunaliella, Nannochloropsis*).

Preferred waste(s) or residue(s) are lignocellulosic wastes or residues from agriculture and wastes or residues from pulp and paper industry processes including cellulosic (energy) crops.

Preferred waste(s) or residue(s) are also biowaste from institutional kitchen or from food or feed industry.

Preferred waste(s) or residue(s) are also microbial wastes or residues, in particular algae or bacterial waste or residues. Organic waste or residue material refers in particular to any organic waste or residue, which *Streptomyces* can use for growth and/or for lipid production.

In some embodiments of the invention organic wastes or residues can be supplemented with an additional carbon source, such as glycerol, a fraction from sugar or starch industry, sugar or starch syrup(s) or purified sugar(s) or any mixtures thereof. More specifically organic wastes or residues can be supplemented with crude products from sugar and starch industry, such as sugar syrups, starch syrups, glucose (dextrose) syrups or molasses. Further, the wastes can be supplemented with single or mixes of purified C6 or C5 sugar(s) such as glucose, fructose, mannose, xylose or arabinose, sugars dimers such as sucrose or lactose or sugar polymers such as cellulose, starch or xylan. The use of supplements from sugar or starch industry or other purified sugars may increase and accelerate the growth of *streptomycetes* and/or lipid accumulation.

The term organic waste or residue encompasses also the term "waste or residue fraction". The term "waste or residue fraction" refers, for example, to waste produced as a side (branch) product or side (branch) product from an industrial process producing some other product as the main product.

Within the scope of the present invention is the use of organic wastes or residues alone or in any combination or mixture.

In terms of lipid accumulation in the cultivations it is advantageous to use waste or residue to starch syrup or sugar syrup in the ratio from 10/1 to 1/2, preferably from 5/1 to 1/1. For example, good accumulation of lipids was found in cultivations containing 10-50 g/l of waste with 10 g/l of sugar syrup.

Furthermore, as described herein, it is beneficial for cell growth to supplement industrial organic waste or residue material with microbial residues, such as cell debris. As herein described good growth was found for example in cultivations where cell debris, in particular from bacterial or algal origin was used together with organic waste material, such as CSL (Corn Steep Liquor), and/or with Farmamedia as medium supplement. For example, bacterial debris from *streptomycetes* or *lactobacilli* and/or algae debris from *Phaeodactylum, Chlorella, Dunaliella* and *Nannochloropsis* can be used in the invention. Another beneficial supplement to cell growth according to this invention is soya.

Starch is advantageous to accumulation of lipids. However, economically it is of benefit, if starch is replaced by agricultural residues, such as bagasse, bran, chaff or straw. Algae or microbial cells or residues, such as bacterial or algae debris, biowaste, meat, CSL, OVR (grain (barley) protein feed), mink feed, and/or offal can replace the protein based ingredients typically useful in *streptomycetes* fermentation, such as yeast extract, Farmamedia, and/or soya.

In the cultivation media waste or residue in a wide scale can be used. In some embodiments the amount of waste or residue in the cultivation media can vary from 1 g/l to 400 g/l, typically from 2 g/l up to 200 g/l, in some embodiments from 20 to 150 g/l, in some other embodiments from 50 to 100 g/l. *Streptomycetes* have been found to use waste fractions effectively for growth and the accumulation of lipids has been found to be similar when compared to cultivations with pure nutrients.

As described herein the microbial cell growth may be followed by using Package Mycelia Volume (PMV), cell mass changes, plating, microscopy and visual analyses.

High density cell growth is obtained with several waste fractions. In various embodiments it varies from 1 to 200 g/l, typically from 10 to 130 g/l as dry cell mass.

The PMV values with several waste fractions varies from 1% to 80%, typically from 6% to 40% in the standard cultivation conditions (28° C., 150 rpm).

It is, however, clear that even higher cell densities can be obtained by adjusting the fermentation conditions accordingly. On the other hand cell mass does not directly correlate with the amounts of lipids accumulated.

Within the scope of the present invention is also the use of waste material in combination with pure ingredients.

Hydrolysed or partially hydrolyzed (depolymerised) organic waste(s) or residue(s) are useable in the present invention. Wastes or residues can be hydrolysed by (thermo) mechanical, chemical or enzymatic hydrolysis. For example, waste or residue material can be treated by suitable enzymes to digest crude ingredients. Suitable enzymes are for example cellulases, hemicellulases, xylanases and pectinases. Also *streptomycetes* possessing both digestive enzyme functions and having capability to accumulate lipids can be used in the invention. Hence, preprocessing of the waste is not necessary. For example suitable strains for this purpose are those belonging to *S. roseosporus* and *S. albus* species.

Within the scope of the present invention are, batch, fed-batch and continuous cultivations.

In cultivations with solid or semisolid substances as raw materials (carbon and/or nutrient sources), biomass may decrease in the first days of cultivation due to the utilization of raw materials by microorganisms increasing in the following days.

In some embodiments of the invention *Streptomyces* produce lipids as estimated by dry mass of chloroform extracts derived from the cultivations at least 0.1 g/liter, preferably at least 0.5 g/liter, more preferably at least 1 g/liter, still more preferably at least 5 g/liter of the spent cultivation medium, in some embodiments at least 10 g/liter, typically 5-30 g/liter, in some other embodiments 10 to 25 g/liter up to 150 g/liter estimated as dry mass of chloroform extracts. It varies in some embodiments in the range of 1-200 g/liter, being typically 5-100 g/liter of spent cultivation medium.

In some embodiments of the invention the concentration (titre) of TAGs is generally at least 0.1 g/l (0.1 kg/1000 liter), preferably at least 0.5 g/l (0.5 kg/1000 liter), more preferably at least 1 g/liter (1 kg/1000 liter), still more preferably at least 5 g/liter (5 kg/1000 liter) of spent cultivation medium. It usually varies from 0.5 to 150 kg/1000 liter, in some embodiments 1 to 100 kg/1000 liter, in some other embodiments 1 to 70 kg/1000 liter, being typically about 5-50 kg/1000 liter, in some embodiments 10 to 30 kg/1000 liter, in some other embodiments 15 to 25/kg/1000 liter of spent cultivation medium.

The improvement of TAG production by the genetically modified strains is generally at least 10%, typically at least 30%, in some embodiments at least 50% and even 100-300% compared to the parent strains.

"Spent cultivation medium" refers to a medium used in the cultivation of microorganisms and comprising the products accumulated by the microorganisms. Spent cultivation medium comprises solid phase such as biomass, like microorganisms and solid raw materials, as well as liquid phase. Therefore, spent cultivation medium comprises products accumulated inside the microorganism cells and released from the cells to the medium. The spent cultivation (or culture) medium can be called also spent cultivation broth. "Cultivation medium" refers usually to cultivation medium before use (before inoculation and cultivation).

Furthermore, in various embodiments of the invention the amount of total lipids is at least 10% by its weight of dry cell mass, typically it is 20-60% by its weight of dry cell mass.

In various embodiments of the invention the lipid fraction produced by *streptomycetes* comprises mainly of TAGs. This means that at least 30 wt-%, in some embodiments at least 50 wt-%, in some other embodiments at least 80 wt-%, yet in some further embodiments at least 70 wt-%, yet in some further embodiments at least 80 wt-%, or yet in some further embodiments at least 90 wt-% of the lipid fraction is TAGs.

The lipid profile characteristic to a non-modified (parent strain) or genetically modified strain cultivated on pure sugar comprises typically about 70 to 95 wt-% of TAGs and about 5 to 30 wt-% of oligomers, diacylglycerols and monocylglycerols and free fatty acids. The fatty acids of non-modified or genetically modified *Streptomyces* strains comprises typically of branched and straight chain fatty acids. The fraction of branched fatty acids can be between 20 to 80 wt-%, and typically is between 40 to 70 wt-%. The content of methyl-branched fatty acids can be between 45 to 50%. The majority of fatty acids determined were saturated.

Further, *Streptomyces* lipids also contain squalene or squalene derivates typically 2 to 5 wt-%, which can be used as base oils or starting material for base oils for lubricant applications.

Lipid profiles of *Streptomycetes* have been reported in literature by Olukoshi and Packter (1994), by Packter and Olukoshi (1995).

The composition of the lipid profile most likely changes when *Streptomyces* is cultivated on a medium comprising waste(s) or residues(s) instead of pure sugar, because lipid extraction may comprise lipids from the waste (for example membrane phospholipids are extracted).

"Lipids" generally refer here to the lipids produced by *Streptomyces* during the cultivation and to the lipids contained in the components of the culture medium, in particular waste or residue material in the culture medium. "A lipid fraction" refers to a fraction of the lipids, such as TAGs or branched fatty acids or squalenes.

In some embodiments of the invention, cell debris and even algae residues give remarkable quantities of lipids dominating by TAGs. The preferred nutrient and/or C-source of algae are *Chlorella* and *Dunaliella*, which gave the highest quantity of TAGs in the spent cultivation medium.

As described herein, prolonged batch cultivations of the *Streptomyces* strains in waste fractions (typically exceeding 7 days) and in pure ingredients based medium (typically exceeding 5 days) result in disappearance of TAGs and some other lipids, suggesting that lipids are degraded.

In some embodiments of the invention lipase inhibitors may be added to the culture medium. Suitable lipase inhibitors are for example silver ions (Lee & Lee, 2006) or cationic substances (Cote and Sharech, 2008). By using lipase inhibitors it is possible to inhibit degradation of lipids and enhance the accumulation of TAGs. Even small concentration of inhibitors, for example $AgNO_3$ in concentration 0.04 to 0.06 g/l, are useful as is shown in Example 12.

In some embodiments of the invention the inoculation of the cultivation medium is carried out by *streptomycetes mycelia* or spores. In preferred embodiments the inoculation is carried out by using spores. The amount of spores can be $10^7$-$10^9$ spores/one liter (e.g. $5 \times 10^{12}$ spores/500 liter).

In some embodiments of the invention the cultivation can be carried out in 1 to 21 days, typically in 2 to 14 days, preferably in 2 to 6 days. In some embodiments lipase inhibitors may be added in the middle (or after the start or before the end) of the cultivation.

In various embodiments of the invention the cultivation temperature is usually 20 to 36° C., typically it is 26-30° C.

The cultivation of *streptomycetes* for lipid production is typically carried out in various embodiments of the invention in a liquid culture medium in a fermentor preferably under suitable aeration and agitation. The mixing speed varies typically from 0 to 800 rpm, being typically 150-600 rpm.

Figure 3A:
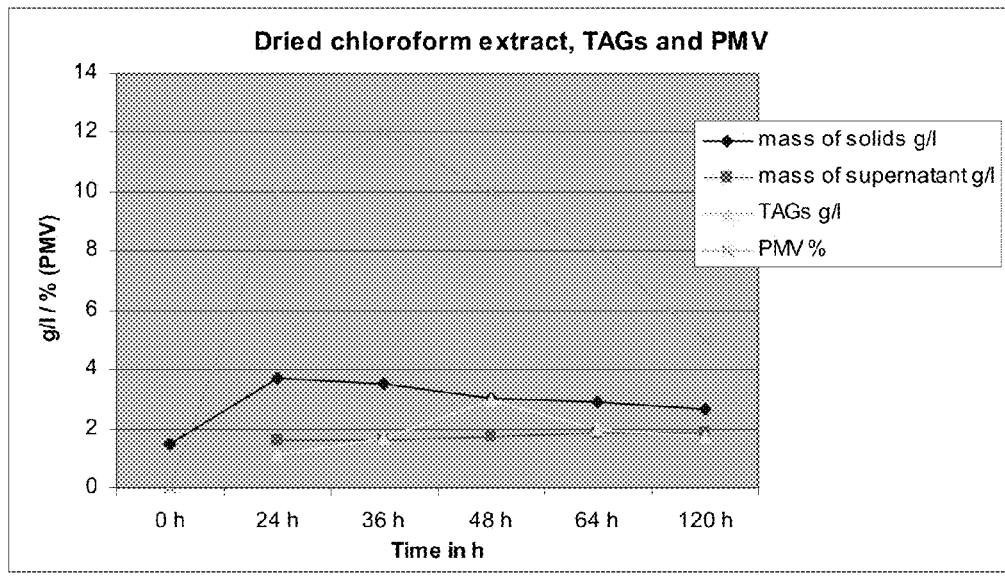
FIG. 3 shows the changes of PMV, cell mass, and dispersion of lipids in solid and liquid fractions in 5 day cultivation of the strain G009 in liquid TSB media. The growth cycle is about 36 hours after which cell lysis takes place. The accumulation of TAGs takes place immediately after the fast growth stage in 24 to 48 hours.
Figure 3B:
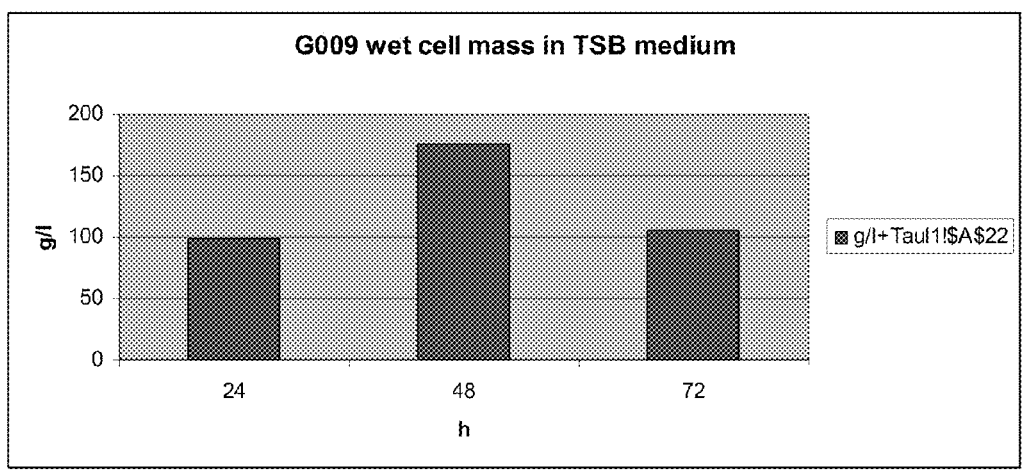

As wastes or residues may contain lipids it is rational to follow up the use of the external lipids to determine the lipids formed by the bacterial strains. As described herein the utilization of external lipids was followed up by changes in solid mass and changes in lipid profiles. It was shown that the biomass decreased up to 36-48 hours from the beginning of the cultivation and started to increase after that. The cycle time is dependent on the degree of processing of waste in use. Nevertheless, no remarkable differences were found after five days of cultivation when cultivation was followed up to 8 days. The lipids were detectable in supernatant in the 0 sample and increased in a solid fraction up to 4-5 days. After that the lipids reduced in the cell fraction, and a part of the lipids were found in supernatant and probably a part of the accumulated lipids were used for metabolism. FIG. 3 demonstrates the follow up of PMV, cell mass and lipids of solid and liquid fractions in 8-day cultivation, It can be concluded that lipids detected after 3 days were derived from bacterial metabolism.

The lipid yields ($g_{lipids}/g_{glucose}$) determined to fed sugar varied in the range of 10-55%. The yields were determined based on the fed pure sugar and did not consider the sugar included in wastes and residues. Theoretical maximum of lipid yield from glucose is 33%. However in practice, the maximum lipid yield is 20-22% (Ratledge and Cohen 2008). Thus, lipid yields higher than 22% indicate that lipids were generated (produced) from waste and residue materials.

*Streptomyces* Strains

By *Streptomyces* bacteria are here meant any species or strains belonging to the genus *Streptomyces*.

Preferred species in various embodiments of the invention are species comprising, preferably are selected from the group comprising, more preferably are selected from the group of *Streptomyces roseosporus, Streptomyces griseus, Streptomyces albus, Streptomyces peucetius, Streptomyces aureofaciens Streptomyces lividans, Streptomyces coelicolor, Streptomyces hygroscopicus, Streptomyces avermitilis*, and *Streptomyces lydicus*. Most preferred species are selected from the group of *Streptomyces roseosporus, Streptomyces griseus, Streptomyces albus, Streptomyces peucetius, Streptomyces milbemycinius* and *Streptomyces aureofaciens*.

More specifically, the *Streptomyces* strain comprises, may be selected from the group comprising, more preferably is selected from the group of *Streptomyces roseosporus* GAL4111, *Streptomyces roseosporus* G011, *Streptomyces griseus* GAL1005, *Streptomyces albus* GAL1001, *Streptomyces peucetius* D2 GAL4082, *Streptomyces peucetius* P55 GAL4081, *Streptomyces aureofaciens* GAL1004, *Streptomyces lividans* GAL1002, *Streptomyces coelicolor* GAL1003, *Streptomyces hygroscopicus* GAL4051, *Streptomyces avermitilis* GAL1006, *Streptomyces lydicus* GAL 1007. Most preferably the strain is selected from the group of *Streptomyces roseosporus* GAL4111, *Streptomyces griseus* GAL1005, *Streptomyces albus* GAL1001, *Streptomyces peucetius* D2 GAL4082, *Streptomyces milbemycinius* GAL4211 and *Streptomyces aureofaciens* GAL1004

It is known that various *streptomycetes* species can accumulate triacylglycerols (TAGS) in small quantities: *S. albus* (Alvarez and Steinbüchel, 2002); *S. lividans* (Packter N D Olukoshi, 1995, Alvarez and Steinbüchel, 2002); *S. coelicolor* (Arabolaza al., 2008, Alvarez and Steinbüchel, 2002); *S. hygroscopicus* (Gesheva et al., 1997); *S. aureofaciens* (Bëhel and Jilek, 1969); *S. griseus* (Suutari et al., 1992, Alvarez and Steinbüchel, 2002); *S. avermitilis* (Kaddor et al., 2009; Novak et al. 1992); and *S. lydicus* (Nagao et al., 1991). The publication by Wältermann et al. (2006) characterizes gene products involved in the biosynthesis of neutral lipids in bacteria. However, the production of lipids by using a typical prior art fermentation process is relatively energy-consuming and thus expensive.

In this disclosure *Streptomyces* bacteria refer in particular to pure cultures of bacteria belonging to genus *Streptomyces*. In some embodiments different *Streptomyces* species or strains in combination can be cultivated subsequently or together. Furthermore, in this disclosure *Streptomyces* bacteria refer in particular to *Streptomyces* species and strains capable of naturally producing lipids. In some embodiments of the invention the capability of *Streptomyces* species or strains can be improved by introducing nucleic acid sequences responsible for lipid production into *Streptomyces* strains and expressing these nucleic acid sequences under regulatory elements, such as a promoter, recognized by the *Streptomyces* host.

It is also possible to improve the *Streptomyces* species or strains used in lipid production by making the host strains deficient in producing endogenous bioactive products, such as lipopeptide antibiotics. This can be carried out by molecular biology methods well known in the art. Useful methods are for example deletion of the gene(s) responsible of producing bioactive product(s) or various mutagenization methods, such as site-directed mutagenesis.

"Making deficient of a gene" refers either to a genetic modification of the *Streptomyces* host to delete or truncate a specific gene or a genetic modification of the *Streptomyces* host resulting in reduced expression of the gene or reduced activity of the gene product by any suitable method. By "inactivation" is meant a genetic modification (usually deletion) resulting in complete loss of activity of a gene product.

From *Streptomyces* strains can be generated mutants not producing desired bioactive products, such as antibiotics. Mutants can be generated for example by random methods using a chemical mutagen, such as NTG, (N-methyl-N'-nitro-N-nitrosoguanidine). Colonies that fail to produce antibiotics can be tested by a suitable assay, such as antibacterial assay. Furthermore, the accumulation of lipids can be analysed for example by HPLC. From *Streptomyces* strains can be generated mutants not producing desired bioactive products, such as antibiotics also by targeted inactivation of certain genes, such as inactivation of the first biosynthetic gene(s) of the bioactive product. This was exemplified by inactivating the polyketide biosynthesis (PKS) genes in a *Streptomyces* host. The gene product was truncated by a biomarker. The clones obtained were studied for expression of antibacterial properties and analyzed for production of milbemycins by HPLC.

In the present invention it was surprisingly found that *Streptomyces* strains can produce significant amounts of lipids without genetic engineering of their lipid synthesis pathway. However, as discussed above, it may be of advantage that the host is made deficient of producing bioactive products, such as lipopeptide antibiotics.

In the present invention it was surprisingly found that *Streptomyces milbemycinius* species was capable of producing high amount of lipids. High lipid production was exemplified in particular with a *S. milbemycinius* strain made deficient of producing antibiotic milbemycins. As is described in the examples a *S. milbemycinius* strain was able to produce lipids 20 g/l or more. The efficiency of conversion of pure glucose or glucose derived from starch was 33%. The amount of TAGs was in the range of 80-90% of all lipids.

In the context of the work resulting in the present invention, the lipid production of *Streptomyces* strains from various *Streptomyces* species and strains was studied. In some *Streptomyces* species and strains the lipid synthesis pathway was genetically modified. These experiments were followed by experiments where the strains were cultivated on media, where waste or residue materials were used as carbon and/or nutrient source. The production of lipids by the strains of *Streptomyces* genus was exemplified by using 11 *Streptomyces* strains. The strains were studied for accumulation of metabolites including lipid fraction, triacyiglycerides referred to as TAGs herein. All tested strains accumulated detectable quantities of TAGs and surprisingly, four out of the 11 tested *Streptomyces* strains were very fast growing giving wet cell mass exceeding 200 g/l in two to three days (see Table 1). These strains were from species *Streptomyces aureofaciens*, *Streptomyces roseosporus*, *Streptomyces griseus* and *Streptomyces albus*. The strains were *Streptomyces aureofaciens* GAL1004, *Streptomyces roseosporus* GAL4111 and the mutant derived from it, G011, *Streptomyces griseus* GAL1005 and *Streptomyces albus* GAL1001. The strains were further cultivated and analyzed for TAG production. Also, the ability of the strains to retain their non-producing character of bioactive metabolites during storage was verified.

As described herein 11 *Streptomyces* strains were cultivated in typical cultivation conditions to enhance the growth and also accumulation of secondary metabolites. The media used were TSB, 2*TY and E05. The cultivation conditions in a shaker were, 28° C., 30° C., and 34° C. with agitation of 150 and 300 rpm.

The content of the cultivation media were:
TSB: 17 g/l pancreatic digest of casein, 3 g/l enzymatic digest of soybean meal, 2.5 g/l dextrose, 5 g/l sodium chloride, 2.5 g/l dipotassium phosphate; 2*TY: 16 g/l of tryptone pepton, 10 g/l yeast extract, 5 g/l NaCl; E05: 20 g/l of dextrose, 20 g/l of starch, 5 g/l of farmamedia, 2.5 g/l of yeast extract, 1 g/l of $MgSO_4 \cdot 7H_2O$, 1 g/l of $KH_2PO_4$, 3 g/l of $CaCO_3$, 3 g/l of NaCl.

Table 1 shows characters of the strains and the relevant results of cultivations done in TSB media. The TAGs were estimated by TLC plate compared to standard.

TABLE 1

| Galilaeus' code | Strain | Characters | Growth time In days (from growth curve) | The highest PMV | Cell mass wet/dry g/l | TAGs (g/l) |
|---|---|---|---|---|---|---|
| GAL1001 | S. albus | Fast growth cycle and easy to cultivate. Non-producer of bioactive metabolites. | 2 | 10 | 275/42 | 0.5 |
| GAL1002 | S. lividans | Fast growth cycle. | 3 | 8 | 102/13 | 0.1 |
| GAL1003 | S. coelicolor | Fast growth cycle. Well-known strain. | 2 | 10 3 days | 127/14 | 0.1 |
| GAL4051 | S. hygroscopicus | Fast growth cycle. | 2 | 10 3 days | 125/13 | 0.1 |
| GAL1004 | S. aureofaciens | Fast growth cycle. | 2 | 16 2 and 3 days | 220/46 | 0.5 |
| GAL1005 | S. griseus | Fast growth cycle. Produces bioactive compounds of different chemical classes. Well-known strain. | 2-3 | 12 3 days | 206/47 | 0.5 |
| GAL4111 | S. roseosporus | Fast growth cycle and easy to cultivate. Produces cyclic lipopeptide where peptide synthesis could be inactivated. | 1 | 10 | 280/40 | 0.5 |
| GAL1006 | S. avermitilis | Fast growth cycle. | 2-3 | 16 | 210/19 | 0.1 |
| GAL1007 | S. lydicus | Fast growth cycle. | 2 | 10 | 112/15 | 0.1 |

TABLE 1-continued

| Galilaeus' code | Strain | Characters | Growth time In days (from growth curve) | The highest PMV | Cell mass wet/dry g/l | TAGs (g/l) |
|---|---|---|---|---|---|---|
| GAL4081 | S. peucetius P55 | Inactivated in production of secondary metabolites (anthracycline) | 5 | 6 | 114/8 | 0.1 |
| GAL4082 | S. peucetius D2 | Inactivated in production of secondary metabolites (anthracycline) | 2 | 10 | 140/18 | 0.5 |

The strains that are able to grow well determined by wet cell mass and/or as PMV-value, and to accumulate detectable levels of lipids in a short cultivation time, are preferable strains for further development concerning strain improvement for lipids accumulation and for development of fermentation conditions.

Genetically Engineered Strains for Enhanced Oil Production

The construction of recombinant hosts (i.e. genetically manipulated strains GMO) producing efficiently lipids was exemplified herein by introducing genes involved in the biosynthesis of lipids into some Streptomyces hosts having the capability of effectively accumulating lipids naturally.

Both the original strains and the clones carrying the genes involved in lipid biosynthesis were cultivated in a large variety of waste and residue materials including biowaste. Unexpectedly, the strains were able to grow and produce lipid fraction on waste or residue fractions with and even without additional carbon source.

Cultivations revealed a fast growth cycle time: the stationary phase was reached in 24 hours or even before while accumulation of lipids continued even up to 6 days thereafter. The dry/wet cell mass in cultivation was not remarkably increased by the clones compared to the parental strain. However, remarkable increase in lipid accumulation, even up to 300% improvement compared to the parent strains was observed, in particular in the main fraction TAGs.

As described herein streptomycetes hosts showing suitable properties for industrial useful bio-fuel fermentation processes can be further improved by any known strain improvement methods, such as natural selection, random mutagenization, and by genetic engineering.

Suitable genes to improve the accumulation of lipids comprise various genes encoding enzymes involved in fatty acid biosynthesis. Suitable genes are in particular gene encoding diacylglycerol acyltransferase (DGAT) (EC 2.3.1.20) and gene encoding 3-ketoacyl-acyl carrier protein synthase III (FabH) (EC 2.3.1.41).

A gene encoding DGAT function (EC 2.3.1.20) is, for example, sco0958 (SEQ ID NO:1), and a gene encoding 3-ketoacyl-acyl carrier protein synthase III (FabH) (EC: 2.3.1.41) is, for example, sco5888 (SEQ ID NO:2). The gene sco0958 (ID101096381) catalyzes the ultimate step in the biosynthesis of TAGs (Arabolaza et al., 2008) and sco5888 (ID101101330) (Li et al., 2005) is responsible for the first elongation step in the biosynthesis of fatty acids. The genes sco5888 and sco0958 originate from S. coelicolor.

Within the scope of the invention are also the closest homologues of said genes sco0958 and sco5888 in various Streptomyces species.

Within the scope of protection are also nucleotide sequences which hybridize to at least one of said genes or said homologues under stringent conditions.

Within the scope of invention are also nucleotide sequences causing the same or an equivalent function as gene products ID 101096381 or ID 101101330.

Within the scope of the present invention are also a nucleotide sequence encoding an amino acid sequence showing at least 60% identity, preferably at least 65%, preferably at least 70%, preferably at least 75%, preferably at least 80%, preferably at least 85%, more preferably at least 90%, still more preferably at least 95%, more and more preferably at least 98% identity to amino acid sequences SEQ ID NO:3 or SEQ ID NO:4.

Within the scope of the present invention are nucleotide sequences causing the same function or equivalent function as said genes sco0958 (ID101096381) and sco5888 (ID 101101330). Such nucleotide sequences may be fragments or derivatives of said genes, the closest homologues of said genes in other Streptomyces species or nucleotide sequences which hybridize to at least one of said genes or said homologues.

The hybridization is preferably carried out under stringent hybridization conditions. Stringent conditions can be defined as hybridization at 65° C. in a low salt concentration, 1.5 mM sodium citrate, pH 7.0 and 0.015 NaCl, according to Boehringer Mannheim's manual, DIG System User's Guide for Filter hybridization.

It is evident that small variations in the nucleotide sequence of a gene do not significantly change the catalytic properties of the encoded protein. For example many changes in the nucleotide sequence do not change the amino acid sequence of the encoded protein. Also an amino acid sequence may have variations, which do not change the functional properties of a protein, in particular they do not prevent an enzyme from carrying out its catalytic function. Such variations in the nucleotide sequence or DNA molecules or in an amino acid sequence are known as "functional equivalents", because they do not significantly change the function of the gene to encode a protein with a particular function, e.g. catalyzing a particular reaction or, respectively, change the particular function of the protein. Within the scope of the present invention are functional equivalents, including fragments or derivatives, or closest homologues of the nucleotide sequence SEQ ID NO:1 or SEQ ID NO:2, or of the amino acid sequences SEQ ID NO 3 or SEQ ID NO:4, respectively.

Streptomyces capable of producing enzymes involved in lipid biosynthesis can be screened, the activity on various substrates can be determined, and the enzyme characterized. Nucleotide sequences encoding enzymes involved in lipid biosynthesis in various organisms can be isolated and the amino acid sequences can be compared with the amino acid sequences SEQ ID NO: 3 and SEQ ID NO:4. A person skilled in the art can also identify a conserved region in the nucleotide or amino acid sequence and clone a gene fragment using PCR techniques. After sequencing the fragment the complete gene can be obtained for example by using cDNA library in a vector. A nucleotide sequence encoding the enzyme can be identified also by nucleic acid hybridization.

Standard molecular biology methods can be used in the cloning of the genes i.e. in the isolation and enzyme treatments of DNA, in *E. coli* transformations, the isolation of a fragment comprising the gene by amplification in a PCR reaction (Coen D M, 2001) and in the techniques for codon change. The basic methods used are described in the standard molecular biology handbooks, e.g. Sambrook et al. (1989) and Sambrook and Russell (2001). Insertion of the nucleotide sequence under a strong promoter in an expression vector, transfer of the vector into suitable host cells and cultivation of the host cells in conditions provoking production of said enzyme. Methods for protein production by recombinant technology in different host systems are well known in the art (Gellissen, 2005).

Genetically modifying a *Streptomyces* host to express an endogenous or exogenous gene can be carried out for example by introducing into a *Streptomyces* host an exogenous gene from another *Streptomyces* species or an additional copy or copies of an endogenous gene. The gene may be expressed under a promoter recognized by the *Streptomyces* host. In some embodiments the gene may be expressed under another promoter resulting in increased expression of the gene. Alternatively the *Streptomyces* host may be genetically modified so that either the gene is more abundantly expressed or that the activity of the gene product is increased.

The term "endogenous gene" refers here to a gene which is natural to the *Streptomyces* host.

The term "exogenous gene" refers here to a gene which is not natural to the *Streptomyces* host.

The "closest homologue of an *S. coelicolor* gene", in other *Streptomyces* species refers here to a gene with the highest percentage of identical nucleotides in sequence alignment of the *S. coelicolor* gene and the genes of the other species; or a gene whose protein product has the highest percentage of identical amino acids to the protein product encoded by the *S. coelicolor* gene. By "closest homologue" is meant in particular a gene or nucleotide sequence having at least 60%, preferably at least 65%, preferably at least 70%, preferably at least 75%, preferably at least 80%, preferably at least 85%, more preferably at least 90%, still more preferably at least 95%, more and more preferably at least 98% nucleotide or amino acid sequence identity compared to a specific *S. coelicolor* gene (SEQ ID NO:1 or SEQ ID NO:2) or product of said gene (SEQ ID NO:3 or SEQ ID NO:4).

The term "identity" refers to the identity between two nucleic acid or amino acid sequences, respectively compared to each other from the first nucleic acid to the last nucleic acid or from the first amino acid encoded by the corresponding gene to the last amino acid. The identity of the full-length sequences can be measured by using Needleman-Wunsch global alignment program at EMBOSS program package (European Molecular Biology Open Software Suite; Rice et al., 2000) The program version can be 2.9.0 and the parameters: EMBLOSUM62, Gap penalty 10.0, Extend penalty 0.5.

"Genetical modification" of a *Streptomyces* host means here any genetic modification method by which a *Streptomyces* host is modified to express a specific endogenous or exogenous gene and/for to be deficient of a specific gene or genes.

Genetical modification methods for a *Streptomyces* host are available and well known for a person skilled in the art and disclosed for example in Kieser et al, 2000.

As described herein a suitable method for introducing a gene into a *Streptomyces* host is for example protoplast transformation.

The vectors for introduction of the gene sequences, typically for example PCR fragments, into the host strains may be selected among any vectors that are able to introduce the cloned fragment into the host strain. Integration vectors, medium copy number and high and low copy number vectors to introduce the fragments into suitable hosts can be successfully used.

Suitable vectors for transferring of the nucleic acid fragments into *Streptomyces* hosts are for example pIJE486 (Ylihonko et al., 1996) and pHJL401 (Kieser et al., 2000).

The most preferred host strains are *streptomycetes* strains shown in Table 1, in particular the strains GAL1001 and GAL4111 or any mutant strains derived from said strains.

Nevertheless, it is advantageous to use mutant strains unable to accumulate bioactive compounds in culture broth for commercial production of bio-fuels. For this purpose the most preferred strains are GAL1001 and G011.

As described herein *S. roseosporus* GAL4111 and a derivative thereof deficient in producing endogenous bioactive products, *S. roseosporus* G011, and GAL1001 were genetically modified by using genes involved in the biosynthesis of lipids.

There are several genes involved in lipid metabolism in bacteria. In the present disclosure it has been shown that the genes sco0958 and sco5888 either separately or in combination surprisingly increased the quantities of TAGs accumulated by *streptomycetes*. sco0958 is responsible for the terminal reaction in triacylglyceride (TAG) biosynthesis being an esterification of diacylglycerol (DAG) of a fatty acid molecule (Arabolaza at al., 2008). sco5888 is 3-ketoacyl acyl carrier protein encoding the first elongation step of fatty acid biosynthesis (Li at, 2005). The genes may be cloned using any suitable cloning method. According to one embodiment of the invention the cloning is carried out by PCR from the chromosomal DNA using homologous primers.

The genes were introduced into the said strains by protoplast transformation. The strains carrying these genes separately or in combination showed increased accumulation of TAGS.

The GMO strains selected and designated as G009, G010, G013, G014, G015, G012, G016, G017, and G019 carry an intact plasmid retaining cultivation properties and lipids accumulation after several passages.

The best strains for accumulation of lipid fractions enriched in TAGs were the clones derived from GAL1001, designated as G009, G013 and G017.

As described herein the vectors pIJE486 (Ylihonko et al., 1996) and pHJL401 (Kieser et al., 2000) were used to introduce genes sco0958 and sco5888 into *Streptomyces* hosts GAL1001, GAL4111 and G011. In Example 2 Table 3 shows the codes used for the genetically modified strains. All the strains produced more lipids as compared to the parent strains. The cultivations were carried out in temperatures ranging from 20 to 36° C., agitation varying from 0 to 800 rpm, and pH 5-8.5.

The GMO strains G009, G010, G013, G014, G015, G012, G016, G017, and G019 with their parent strains, GAL1001, GAL4111 and G011, as controls were cultivated in a wide variety of cultivation media. The lipid yield was estimated as $(g_{lipids}/g_{glucose})*100$. The parent strains GAL1001 and G011 produced lipids as estimated by dry mass of chloroform extracts and by TLC analysis referring to standards to be 0.1-0.5 g/l of the cultivation broth, respectively. The chloroform extracts of cell fractions of the transformants gave a mass in the range of 5.9-25.2 g/l while the TAG content was estimated as 3 to 23 g/l. The best improvement was obtained by G009. Surprisingly, the lipid fraction on TLC was very similar in all trans-formants and >70% of detectable lipids was in TAG fraction.

In the above calculations the sugar content was calculated to be 10 g/l in the tested media containing Corn Steep Liquor 20 g/l, Nutrisoy 10 g/l and Dextrose syrup 10 g/l. The cultivations were carried out in flasks for 5 days at 28° C., 150 rpm, lipids were extracted from the cells and supernatant separately with equal volume of chloroform-Methanol (2:1) by shaking for 1 hour. A sample of chloroform fraction was applied on TLC plate and a chloroform fraction was evaporated to dryness for mass determination.

In order to the lipid composition obtained to be suitable for further processing in the manufacture of biofuel, the chemical nature of these compounds is critical. Though different forms of fats are suitable for chemical processing for biofuel production the preferred compounds are TAGs. There are several known methods to further characterize the metabolites in addition to TLC (thin layer chrometograpghy) analytics, for example GC (gas chromatography). GC analysis can be carried out by a standard procedure (ISO15304). HPLC can be used to determine the glyceride lipid profile of the strains. For example, the lipid profile characteristic to a parent strain (exemplified by GAL1001) and to a genetically modified strain (exemplified here by G009) is given in the Table 2.

TABLE 2

Glyceride profile of lipids as percentage value derived from GAL1001 and G009 as analyzed by HPLC.

| The nature of lipids | GAL1001 | G009 |
|---|---|---|
| TAGs | 95 | 88.6 |
| Oligomers | N.A. | 5.2 |
| Diacylglycerols | N.A: | 4.3 |
| Monoacylglycerols | N.A. | 0.3 |
| Free fatty acids | 5 | 1.7 |

*N.A. = not available

Majority of Lipids in *Streptomycetes* Consisted of Triglycerides,

TABLE 3

Examples of fatty acid distribution (% from total fatty acids) of *S. roseosporus* GAL4111 and *S. albus* GAL1001 as determined by GC-MS. The said strains were cultivated for 2 days in cell waste medium; 10 g/l of CSL and 50 g/l of cell waste (cell debris of streptomycetes) without additional supplements at 28° C., 150 rpm.

| | GAL4111 | GAL1001 |
|---|---|---|
| n-C10:0 | 0.02 | 0.03 |
| n-C10:1 | 0.01 | 0.00 |
| iso-C11:0 | 0.03 | 0.00 |
| anteiso-C11:0 | 0.06 | 0.00 |
| n-C11:0 | 0.05 | 0.07 |
| iso-C12:0 | 0.23 | 0.28 |
| anteiso-C12:0 | 0.09 | 0.09 |
| n-C12:0 | 0.11 | 0.12 |
| iso-C13:0 | 0.25 | 0.29 |
| anteiso-C13:0 | 0.45 | 0.55 |
| n-C13:0 | 0.15 | 0.10 |
| n-C13:1 | 0.00 | 0.00 |
| iso-C14:0 | 6.41 | 7.32 |
| anteiso-C14:0 | 0.27 | 0.33 |
| n-C14:0 | 1.25 | 1.03 |
| n-C14:1 | 0.06 | 0.00 |
| iso-C15:0 | 3.94 | 4.34 |
| anteiso-C15:0 | 13.20 | 14.66 |

TABLE 3-continued

Examples of fatty acid distribution (% from total fatty acids) of *S. roseosporus* GAL4111 and *S. albus* GAL1001 as determined by GC-MS. The said strains were cultivated for 2 days in cell waste medium; 10 g/l of CSL and 50 g/l of cell waste (cell debris of streptomycetes) without additional supplements at 28° C., 150 rpm.

| | GAL4111 | GAL1001 |
|---|---|---|
| n-C15:0 | N.A. | N.A. |
| n-C15:1 | 0.85 | 0.30 |
| iso-C16:0 | 16.98 | 18.65 |
| anteiso-C16:0 | 0.11 | 0.13 |
| n-C16:0 | 14.78 | 14.30 |
| n-C16:1 | 4.05 | 2.79 |
| iso-C17:0 | 1.40 | 1.37 |
| anteiso-C17:0 | 4.67 | 4.92 |
| n-C17:0 | 0.61 | 0.58 |
| n-C17:1 | 3.40 | 3.43 |
| iso-C18:0 | 0.29 | 0.25 |
| n-C18:0 | 1.78 | 1.54 |
| n-C18:1 | 8.52 | 8.44 |
| n-C18:2 | 13.06 | 11.43 |
| n-C18:3 | 0.79 | 0.63 |
| n-C19:1 | 0.47 | 0.46 |
| n-C20:0 | 0.20 | 0.19 |
| n-C22:0 | 0.71 | 0.99 |
| n-C23:0 | 0.31 | 0.19 |
| n-C24:0 | 0.14 | 0.12 |
| Fatty alcohols | 0.12 | 0.09 |
| Other fatty acids | 0.18 | 0.00 |

* N.A. = Not available

*Streptomycetes* oil was saturated and majority of fatty acids determined (~70%) were saturated. Further, *Streptomycetes* oil contained significant content of methyl-branched fatty acids (45 to 50% in this case).

TABLE 4

Example of lipid composition of *S. roseosprous* GAL4111 and *S. albus* GAL1001 as determined by GC-MS.

| | GAL4111 | GAL1001 |
|---|---|---|
| Fatty acids* | 84.8 | 89.5 |
| Fatty alcohols | 0.3 | 0.1 |
| Squalenes | 4.3 | 2.5 |
| Other lipids | 0.2 | 0.0 |
| Unidentified lipids | 10.3 | 7.9 |

*Fatty acids include the acylglycerols and free fatty acids

Majority of the lipids consisted of fatty acids (included in acylglycerols and free fatty acids). Lipids also contained squalenes (2.5 and 4.3% from total lipids). Squalenes in GAL4111 and GAL1001 composed of squalene, tetrahydrosqualene, dihydrosqualene, (main components), hexahydrosqualene and octahydrosqualene.

According to the present invention, there are several alternatives to cultivate the suitable *Streptomyces* strains for accumulation of lipids. Different conditions including variety of carbon and/or nutrient sources, and growth conditions were tested.

In order to have an industrially feasible process, the strains naturally accumulating lipids, such as G009, G013 and G017, shall be suitable for aerobic fermentation and fermentation process should be cost-efficient. The costs of fermentation process are heavily affected by media components, energy consumption, waste costs and manpower.

Though it is possible to use the medium derived from pure ingredients and for example those described herein, TSB, 2*TY, and E05, it is more cost-efficient to select any waste fraction without separation, hydrolysis, and/or purification of components as raw materials. The requirements are that the bacteria in use are rich in digestive enzymes to facilitate the growth by crude ingredients including in waste. Therefore, the present invention further contemplates the use of industrial waste fraction or a combination of pure ingredients with the waste. As described herein a comprehensive test series was done with a wide variety of organic wastes or residues from industry including agriculture, municipal waste and microbial residue. Methods suitable for use in the present invention for generating free sugars and a source of nutrient to be utilized for growth from waste fractions are those that are generally known such as use of suitable enzymes for digesting of crude ingredients. However, cultivation of bacteria possessing these digestive enzyme functions while having capabilities for accumulation of said lipids are preferable. Suitable strains for this purpose are consequently *S. roseosporus* and *S. albus* strains. Preferred strains are G009, G010, G013, G014, G015, G012, G016, G017 and G019 with their parent strains, GAL1001, GAL4111 and G011.

The strains involved in this disclosure and preferably the strains G009, G010, G013 and G017 may be cultivated on the organic waste(s) or residue(s). The uses of cell debris derived e.g from the foregoing lot are very suitable nutrient sources to produce lipids in a cost-efficient way. In these cultivations the changes in cell mass were detected to lower in the first two to three days increasing 5-20 g/l in the following three to four days. The dry mass of chloroform extracts derived from these cultivations were in the range of 7-65 g/l reflecting the amount of TAGs as 3-23 g/l as analysed on TLC.

All those unit operations and raw materials described in the embodiments of the present invention, either alone or in combination are efficient in production of oils for biofuels. In specific preferred embodiments the process uses strains G009, G010, G013 or G017. The inoculation is preferably carried out by using spores. The amount of spores is advantageously about $10^{10}$ spores/1 liter to $5*10^{12}$ spores/500 liter. The cultivation is preferably carried out for 2 to 6 days. The cultivation temperature is about 28° C. The cultivation is carried out as a batch or fed-batch fermentation. Suitable agitation is used during cultivation. Furthermore, it is recommended to use pasteurization of medium instead of sterilization to avoid high energy consumption. The process can be continued, for example, for 6 days without any supplements or lipase inhibitors, such as silver ions added in low concentration at the $6^{th}$ day of cultivation. In the end of the cultivation the cell mass is harvested. It is typically about 65 kg/500 l batch. The lipids are recovered from the cell biomass or culture broth by a suitable method. The yield with solvent based extract or by physical scattering is typically at least 5 kg TAGs per 1000 liter spent cultivation medium, typically 10 to 70 kg TAGs per 1000 liter, usually about 30 kg of TAGs from 1000 l batch.

Recovery of Oil

In various embodiments of the invention, oil, or precursors for oil, may be recovered from cell biomass or culture broth using any method known in the art or developed in the future. For example, bacteria may be separated from the medium using a filtration or decanting techniques. Alternatively, centrifugation with industrial scale commercial centrifuges of large volume capacity may be used to separate the desired products.

In some embodiments of the invention, bacterial cells may be disrupted to facilitate the separation of oil and other components. Any method known for cell disruption may be used, such as ultrasonication, osmotic shock, mechanical shear force, cold press, thermal shock, enzyme-catalyzed or self-directed autolysis. Oil can be recovered from cells by extraction with organic solvents or by any method known in the art or developed in the future.

The strains, methods, cultivation conditions, ingredients for fermentation and the process scheme disclosed and claimed herein concern technology that supports large scale and economical cultivation of *Streptomyces* bacteria. This technology is useful to support industrial manufacturing of the various related products. This technology may be of use to economically support the massive cultivation and harvesting of *streptomycetes*.

Production of Biofuel

The lipids produced with the method described herein can be used as feedstock for the production of biodiesel, renewable diesel, jet fuel or gasoline. Biodiesel consists of fatty acid methyl esters, and is typically produced by transesterification. In transesterification, the acylglycerols are converted to long-chain fatty acid alkyl (methyl, ethyl or propyl) esters. Renewable diesel refers to fuel which is produced by hydrogen treatment (hydrogenation or hydroprocessing) of lipids. In hydrogen treatment, acylglycerols are converted to corresponding alkanes (paraffins). The alkanes (paraffins) can be further modified by isomerization or by other process alternatives. Renewable diesel process can also be used to produce jet fuel and/or gasoline. In addition, cracking of lipids can be performed to produce biofuels. Further, lipids can be used as biofuels directly in certain applications.

The *Streptomyces* lipids are beneficial for the production of biofuel. *Streptomyces* fatty acids typically contain methyl-branched chain fatty acids, which are beneficial for biofuel and lubricant applications. Branched fatty acids have a broader liquidity range, making them of interest for low-temperature applications and their low surface tension causes good spreadability (Gunstone et al. 2007). Fatty acid branching improves the cold properties of biofuels, such as biodiesel or renewable diesel. The *Streptomyces* oil has relatively high saturation degree (contains high amounts of saturated fatty acids). This property is an advantage especially for the renewable diesel process, since fatty acid saturation decreases the amount of hydrogen needed in hydrogenation. High saturation degree of lipids may also improve the stability and storability of oil, and reduce the need of antioxidants in oil storage. Further, the main fatty chain lengths are mainly from C14 (14 carbons) to C18 (18 carbons), which is advantageous for the utilization in diesel applications.

Lipids produced with the method can be used as base oils for lubricants (lubrication oils) or as a starting material for production of base oils for lubricants. *Streptomyces* oil contain squalene or squalene derivates (Gräfe et al. 1985; Olukoshi and Packter 1994). Especially, squalene and squalene derivates are suitable for uses in lubricant applications. However, other lipids by *Streptomyces* can be used for lubricant applications as well.

Biofuel which comprises the lipid composition produced according to the present disclosure may comprise advantageous properties for biofuel use. Such properties include for example fatty acid branching which improves cold properties.) Fatty acid saturation is advantageous especially for renewable diesel production.

Deposited Microorganisms

*Streptomyces* sp. G011 strain was deposited under Budapest Treaty on 15 Dec. 2009 to DSMZ-Deutsche Sammlung for Mikroorganismen and Zellkulturen GmbH, and it received the Accession number DSM 23182. Biological material deposited under accession number DSM 23182 at DSMZ-Deutsche Sammlung för Mikroorganismen and Zellkulturen GmbH by Galilaeus Oy of Kairiskulmantie 10, 20781 Kaarina, Finland. Galilaeus Oy authorises the applicant to refer to the aforesaid biological deposit in the present application and applications/patents claiming priority from this application, and gives his unreserved and irrevocable consent to the deposited material being made available to the public in accordance with the applicable national laws.

The other strains presented herein show identical features to the strains available in commercial culture collections as shown in Table 5. The strains as listed in Table 5 were first identified according to their secondary metabolites when available, a partial sequence of 16SrDNA and by comparison of colony morphology. The sequence identity of GAL1001, GAL1002, GAL1003, GAL4051, GAL1004, GAL1005, GAL4111, GAL1006, GAL1007, GAL4081, GAL4082 in the DNA fragment of about 1.4 kb has been >98% to the corresponding sequences of the Strains indicated in Table 5. The sequences used in comparison are found in Gene Banks.

TABLE 5 shows identification of the strains

| Galilaeus' code | Strain | Corresponding Strain with collection number | 16S ribosomal RNA gene code | 16S ribosomal RNA gene length |
|---|---|---|---|---|
| GAL1001 | S. albus | DSM 40313 | GI: 219878476 | 1499 bp |
| GAL1002 | S. lividans | NRRL B16148 | GI: 66379295 | 1449 bp |
| GAL1003 | S. coelicolor | DSM 40233 | GI: 220961405 | 1396 bp |
| GAL4051 | S. hygroscopicus | NRLL 5491 | GI: 228480526 | 1385 bp |
| GAL1004 | S. aureofaciens | DSM 40731 | GI: 284022440 | 1402 bp |
| GAL1005 | S. griseus | ATCC 13273 | GI: 196128028 | 1428 bp |
| GAL4111 | S. roseosporus | NRRL 11379 | GI: 195979310 | 1431 bp |
| GAL1006 | S. avermitilis | NRRL 8165 | GI: 162960844 | 1529 bp |
| GAL1007 | S. lydicus | ATCC 25470 | GI: 219846852 | 1481 bp |
| GAL4081 | S. peucetius P55 | comparable to S. peucetius P55#SnorO; DSM 19075 | GI: 219857135 | 1486 bp |
| GAL4082 | S. peucetius D2 | * | GI: 219857135 | 1486 bp |
| GAL4211 | S. milbemycinius | NRRL5739 | GI91178060 | 1457 bp |

* Studies on a second and third ring cyclization in anthracycline biosynthesis. J. Anti-biot (Tokyo), 2003 Feb; 56(2): 143-53

The strains were identified with 16SrDNA sequences obtained by PCR using the homologous primers:

```
UNIfor    5' GGTGGAGCATGTGGTTTA 3' (SEQ ID NO: 5)
UNIrev    5' CCATTGTAGCACGTGTGT 3' (SEQ ID NO: 6)
```

Various embodiments of the invention are described below with the aid of the following numbered clauses 1-36:
1. A process for producing lipids for biofuel or lubricant, which comprises
   cultivating bacterial cells of the genus *Streptomyces* in a medium comprising organic waste(s) or residue(s) or mixtures thereof as carbon and/or nutrient source(s);
   recovering the lipids from the cells or from the culture medium.
2. The process according to clause 1, wherein the organic waste(s) or residue(s) or mixtures thereof are used as main source(s) of carbon and/or nutrient.
3. The process according to clause 1 or 2, wherein the amount of waste or residue in the cultivation medium is 1 g/l to 600 g/l, typically 1 g/l to 400 g/l, usually 2 g/l to 400 g/l, typically 2 g/l to 200 g/l.
4. The process according to any one of clauses 1 to 3, wherein the organic waste(s) or residue(s) comprise(s) industrial organic waste(s) or residue(s), agricultural organic waste(s) or residue(s), municipal waste(s) or microbial waste(s) or residue(s), or any mixtures thereof.
5. The process according to any one of clauses 1 to 4, wherein the cultivation medium comprises as an additional carbon source glycerol, a fraction from sugar or starch industry, sugar or starch syrup(s) or purified sugar(s) or any mixtures thereof.
6. The process according to any one of clauses 1 to 5, wherein the ratio of waste or residue to starch syrup or sugar syrup is 10/1 to 1/2, preferably 5/1 to 1/1.
7. The process according to any one of clauses 1 to 6, wherein the amount of triacylglycerols in the spent culture medium is at least 1 g/liter, preferably 5 g/liter.
8. The process according to any one of clauses 1 to 7, wherein the produced lipids comprise mainly triacylglycerols.
9. The process according to any one of clauses 1 to 8, wherein the produced lipids are transesterified to produce biodiesel or hydrogen treated to produce renewable diesel.
10. The process according to any one of clauses 1 to 9, wherein the cultivation medium is not sterilized or is pasteurized.
11. The process according to any one of clauses 1 to 10, wherein the cultivation medium comprises lipase inhibitors.
12. The process according to any one of clauses 1 to 11, wherein the cultivation is carried out as a batch or as a fed-batch fermentation.
13. The process according to any one of clauses 1 to 10, wherein the *Streptomyces* species is selected from the group of *Streptomyces roseosporus, Streptomyces griseus, Streptomyces albus, Streptomyces peucetius, Streptomyces aureofaciens Streptomyces lividans, Streptomyces coelicolor, Streptomyces hygroscopicus, Streptomyces avermitilis, Streptomyces milbemycinius* and *Streptomyces lydicus*.
14. The process according to clause 13, wherein the *Streptomyces* strain is selected from the group of *Streptomyces roseosporus* GAL4111, *Streptomyces roseosporus* G011, *Streptomyces griseus* GAL1005, *Streptomyces albus* GAL1001, *Streptomyces peucetius* D2, GAL4082, *Streptomyces peucetius* P55 GAL4081, *Streptomyces aureofaciens* GAL1004, *Streptomyces lividans* GAL1002, *Streptomyces coelicolor* GAL1003, *Streptomyces hygroscopicus* GAL4051, *Streptomyces avermitilis* GAL1006, *Streptomyces milbemycinius* GAL 4211 and *Streptomyces lydicus* GAL1007.
15. The process according to any one of clauses 1 to 14, wherein the *Streptomyces* host is genetically modified to express an endogenous or exogenous gene encoding DGAT (EC 2.3.1.20) and/or 3-ketoacyl-acyl carrier protein synthase UI (FabH) (EC: 2.3.1.41).

16. The process according to any one of clauses 1 to 15, wherein the *Streptomyces* host is genetically modified to express one or more of genes selected from the group of
(a) sco0958 (SEQ ID NO:1) and/or sco5888 (SEQ ID NO:2);
(b) the closest homologue of said genes in a *Streptomyces* species;
(c) a nucleotide sequence which hybridizes to at least one of said genes or said homologues at 65° C. in 1.5 mM sodium citrate, pH 7.0 and 0.015 NaCl;
(d) a nucleotide sequence causing the same or an equivalent function as gene products ID 101096381 or ID 101101330 have;
(e) a nucleotide sequence encoding an amino acid sequence showing at least 60% identity to SEQ ID NO: 3 or SEQ ID NO:4.

17. The process according to any one of clauses 1 to 16, wherein the *Streptomyces* host is made deficient in producing bioactive metabolites, such as antibiotic agents.

18. The process according to any one of clauses 1 to 17, wherein the *Streptomyces* strain is selected from the group of G009, G010, G013, G014, G015, G012, G016, G017, and G019.

19. A *Streptomyces* culture for lipid production, which comprises
(a) a population of bacteria of the genus *Streptomyces*; and
(b) a culture medium comprising organic waste(s) or residue(s) or mixtures thereof as carbon and/or nutrient source(s).

20. The culture according to clause 19, wherein the organic waste(s) or residue(s) or mixtures thereof are used as main source(s) of carbon and/or nutrient.

21. The culture according to clause 20, wherein the amount of triacylglycerols in the spent culture medium is at least 1 g/liter, preferably 5 g/liter.

22. The process according to clause 20 or 21, wherein the produced lipid fraction comprises mainly triacylglycerols.

23. The culture according to any one of clauses 20 to 22, wherein the cultivation medium comprises lipase inhibitors.

24. The culture according to any one of clauses 20 to 23, wherein the cultivation medium is not sterilized or is pasteurized.

25. The culture according to any one of clauses 20 to 24, wherein the *Streptomyces* species is selected from the group of *Streptomyces roseosporus, Streptomyces griseus, Streptomyces albus, Streptomyces peucetius, Streptomyces aureofaciens Streptomyces lividans, Streptomyces coelicolor, Streptomyces hygroscopicus, Streptomyces avermitilis, Streptomyces milbemycinius* and *Streptomyces lydicus*.

26. The culture according to clause 25, wherein the *Streptomyces* strain is selected from the group of *Streptomyces roseosporus* GAL4111, *Streptomyces roseosporus* G011, *Streptomyces griseus* GAL1005, *Streptomyces albus* GAL4001, *Streptomyces peucetius* D2, GAL4082, *Streptomyces peucetius* P55 GAL4061, *Streptomyces aureofaciens* GAL1004, *Streptomyces lividans* GAL1002, *Streptomyces coelicolor* GAL 1003, *Streptomyces hygroscopicus* GAL4051, *Streptomyces avermitilis* GAL1006, *Streptomyces milbemycinius* GAL4211 and *Streptomyces lydicus* GAL1007.

27. The culture according to any one of clauses 20 to 26, wherein the *Streptomyces* host is genetically modified to express at least one gene of the lipid synthesis pathway.

28. The process according to any one of clauses 20 to 27, wherein the *Streptomyces* host is genetically modified to express an endogenous or exogenous gene encoding DGAT (EC 2.3.1.20) and/or 3-ketoacyl-acyl carrier protein synthase III (FabH) (EC: 2.3.1.41).

29. The process according to any one of clauses 20 to 28, wherein the *Streptomyces* host is genetically modified to express one or more of genes selected from the group of
(a) sco0958 (SEQ ID NO:1) and/or sco5888 (SEQ ID NO:2);
(b) the closest homologue of said genes in a *Streptomyces* species;
(c) a nucleotide sequence which hybridizes to at least one of said genes or said homologues at 65° C. in 1.5 mM sodium citrate, pH 7.0 and 0.015 NaCl;
(d) a nucleotide sequence causing the same or an equivalent function as gene products ID 101096381 or ID 101101330 have;
(e) a nucleotide sequence encoding an amino acid sequence showing at least 60% identity to SEQ ID NO: 3 or SEQ ID NO:4.

30. The culture according to any one of clauses 20 to 29, wherein the *Streptomyces* host is deficient in producing bioactive metabolites, such as antibiotic agents.

31. The culture according to any one of clauses 20 to 30, wherein the *Streptomyces* strain is selected from the group of strains G009, G010, G013, G014, G015, G012, G016, G017, and G019.

32. A *Streptomyces* host genetically modified to express an endogenous or exogenous gene encoding DGAT activity (EC 2.3.1.20) and/or 3-ketoacyl-acyl carrier protein synthase III (FabH) (EC: 2.3.1.41), or a nucleotide sequence causing the same or an equivalent function as gene products ID 101096381 or ID 101101330 have.

33. The host according to clause 32, wherein host cell is selected from the group of species of *Streptomyces roseosporus, Streptomyces griseus, Streptomyces albus, Streptomyces peucetius, Streptomyces aureofaciens, Streptomyces lividans, Streptomyces hygroscopicus, Streptomyces avermitilis, Streptomyces lydicus*, preferably selected from the group of species comprising *Streptomyces roseosporus, Streptomyces milbemycinius* and *Streptomyces albus,*

34. The host according to clause 32 or 33, wherein the host is genetically modified to express one or more of genes selected from the group of
(a) sco0958 (SEQ ID NO:1) and/or sco5888 (SEC) ID NO:2);
(b) the closest homologue of said genes in a *Streptomyces* species;
(c) a nucleotide sequence which hybridizes to at least one of said genes or said homologues at 65° C. in 1.5 mM sodium citrate, pH 7.0 and 0.015 NaCl;
(d) a nucleotide sequence causing the same or an equivalent function as gene products ID 101096381 or ID 101101330 have;
(e) a nucleotide sequence encoding an amino acid sequence showing at least 60% identity to SEQ ID NO: 3 or SEQ ID NO:4.

35. The host according to any one of clauses 32 to 34, wherein the strain is selected from the group of strains G009, G010, G013, G014, G015, G012, G016, G017, and G019.

36. A lipid composition produced according to any one of clauses 1 to 15.

37. Use of the lipids or lipid composition produced according to any one of clauses 1 to 15 or the lipid composition according to clause 36, or a fraction of the lipids or lipid composition as biofuel and/or lubricant, or as a starting material for biofuel and/or lubricant production.

38. Use of the lipids or lipid composition produced according to any one of clauses 1 to 15 or the lipid composition according to clause 36 s for the production of biodiesel or renewable diesel.
39. Biofuel which comprises the lipids or lipid composition produced according to any one of clauses 1 to 15, or the lipid composition according to clause 36, or a fraction of lipids or lipid composition, and optionally suitable additives for biofuel use.
40. Lubricant which comprises the lipids or lipid composition produced according to any one of clauses 1 to 15, or the lipid composition according to clause 36, or a fraction of lipids or lipid composition, and optionally suitable additives for lubricant use

EXAMPLES

The following methods for analysis were used in the experiments involved in Examples if not otherwise stated in the text.
Methods:
Detection of Wet Cell Mass:
  Wet cell mass was measured by taking 10 ml sample of culture broth to a tared Falcon tube and centrifuged for 10 minutes at 4000 rpm. After centrifugation supernatant was discarded and Falcon tube was weighted to get mass of cell fraction. The cell mass was given as grams per 1 liter of the culture broth.
Detection of Dry Cell Mass:
  Wet cell mass was dried at 70° C. for two days after which mass was determined by weighing. The cell mass was given as grams per 1 liter of the culture broth.
Detection of PMV:
  Package Mycelia Volume was measured by taking 10 ml of culture broth and centrifuged for 10 minutes at 4000 rpm after which volume of cell phase was measured as % figure.
Visual Analysis of Culture:
  The bacterial cultures were visually analysed by separated colonies on agar plate, by studying liquid cultures and by microscopic analysis.
TLC Analysis:
  5 µg/l of ten times concentrated Chloroform extract was pipetted on TLC plate (Silica gel 60 F254 Merck 1.05729) and run in hexane:diethyl ether:acetic acid (80:20:2). Lipids were coloured with iodine after the run or burned to carbon. Burning of lipids was performed by dipping the plate in 50% $H_2SO_4$ and heating the plate 1 hour in 180° C. Cholesterol (C), cholesterol octadecanat (COD), decanoic acid, glyceryl trimyristate (GTM) and L-α-phospatidylethanolamine were used as standards on TLC. Lipids were visually detected on TLC-plates as yellow (iodine) or black (carbon) spots.
Analysis of TLC Spots:
  Lipids were visually detected on TLC-plates as yellow (iodine) or black (carbon) spots. More clearly iodine coloured spots were seen in UV light. Sample spots were compared with standards to estimate the quantities in g/l. Values (−, +/−, +, ++, +++ or 0-3) were given based on the intensity of the spots if comparison was made between the samples in the same test run.
  Also g/l values of TAGs were estimated by image analysis using Image J program. The standard curve was prepared using concentration scale from 1 g/l up to 40 g/l and the titre of lipids in the culture broth was measured against the standard curve.
Sample Extraction:
  The whole culture broth (solid stage cultivations) or separated mycelia was extracted with an equal volume of chloroform-methanol (Clf-MeOH; 2:1). Tubes were incubated in a shaker at RT for 1 hour. After centrifugation sample was taken from the extract and analysed by TLC and/or by GC.
Detection of Dry Extraction Weight:
  Dry extract weight was determined by drying 1-5 ml of extract at RT for one day in air blow after which mass was determined by weighing. The mass was given as grams per 1 liter of the culture broth.
Bioassay for Antibiotic Production:
  The indicator microorganism was cultivated in TSB broth at +30° C. overnight. The cell stock was diluted 1:100 (v/v) to TSB soft agar. Equal amounts of TSB soft agar (10 ml) were transferred on top of TSB agar plates and the soft agar layer was let to solidify. Small discs of the mutant and control cultures or ethyl acetate extractions (1:1) were transferred on top of the plates. The plates were incubated at +37° C. overnight. The clear halos formed by the mutants were compared to the corresponding halos of the control cultivation.
HPLC Method in Brief:
Equipments:
  Apparatus: Agilent 1100-series chromatography system (A312-319)
  Detector: Agilent UV-VIS-detector (G1315A)
  Column: Zorbax SB-C8, 4.6*150 mm, 3.5 µm
Run Parameters:
  Eluents: Eluent A 2000 ml PW
    Eluent B 2000 ml MeCN
  Column temperature: 60° C.
  Flow rate: 1.5 ml/min
  Run time: 15 min
  Injection: 5 µl/l+needle wash (1:1 PW+MeOH)
  Detection: 240 nm

| Time | Eluent A | Eluent B | Flow |
|---|---|---|---|
| 0.00 | 31% | 69% | 1.5 ml/min |
| 10.00 | 31% | 69% | 1.5 ml/min |
| 10.01 | 5% | 95% | 1.5 ml/min |
| 13.00 | 5% | 95% | 1.5 ml/min |
| 13.01 | 31% | 69% | 1.5 ml/min |

Example 1

Screening of *Streptomycetes* for Accumulation of Lipids

*Streptomyces* species from the local culture collection (Table 1) were tested for growth on standard cultivation conditions to elucidate the cycle time, cell mass and accumulation of lipids. The strains were cultivated in typical broth, in tryptone soy broth TSB (Difco) for two to three days in a shaker (100-330 rpm, 26-34° C.). The following strains were found to give a high cell mass and accumulation of lipids in remarkable quantities in the standard cultivation conditions: GAL4111 (*Streptomyces roseosporus*), GAL1005 (*Streptomyces griseus*), GAL1001 (*Streptomyces albus*) and GAL4082 (*Streptomyces peucetius* D2).

An aliquot of the spore suspension or a loop of mycelia of each strain was used to inoculate 50 ml of TSB medium in 250 ml Erlenmeyer flask. Incubation with shaking was allowed to continue for three days and a sample of 10 ml was taken in each day of cultivation, e.g. in 24 hours intervals. The following characters were analyzed: determination of the wet and dry cell mass, PMV, pH follow up and visual analysis by sampling to define the growth cycle, extraction of lipids fraction in chloroform and TLC analysis of the chloroform extracts.
Typical Cultivation Conditions:
Temperature: 22-36° C.
pH: 5.0-8.5
agitation: 100-330 rpm (¾-1 inch throw)
inoculum form: vegetative mycelia, substrate mycelia, spores
transferring rate: 0.5-50%
standard medium in use: TSB, 2*TY, E05
TSB is Tryptone Soya Broth from Difco containing 17 g/l pancreatic digest of casein, 3 g/l enzymatic digest of soybean meal, 2.5 g/l dextrose, 5 g/l sodium chloride, 2.5 g/l dipotassium phosphate; 2*TY contain 16 g/l of tryptone pepton, 10 g/l yeast extract, 5 g/l NaCl, and E05 contains the following ingredients: 20 g/l of dextrose, 20 g/l of starch, 5 g/l of farmamedia, 2.5 g/l of yeast extract, 1 g/l of $MgSO_4 \cdot 7H_2O$, 1 g/l of $KH_2PO_4$, 3 g/l of $CaCO_3$, 3 g/l of NaCl.
Characters of the Streptomyces Culture:
Time for exponential growth: 12-64 h
Time to accumulate lipids: 24-64 h
The main fraction of lipids: TAGs
The content of TAG in metabolite fraction as estimated by TLC: 20-80%
The oil content in extract as measured by GC is 25-80%, the content of TAGS is 50-95% in oil fraction
The mass of chloroform extract: >10 g/l of culture broth
The TAG fraction of chloroform extract: 10-80%
Wet cell mass: >100 g/l
Dry cell mass: >8 g/l
The range of PMV: 6-16%
Increase of TAGs (highest amount−zero sample) by Image J: 3 g/l (time for highest value 3 days)

Example 2

Construction of Genetically Modified Strains

Two strains, GAL4111 and GAL1001 were used as the hosts of genetic engineering though the same methods are useful for GAL005 and GAL4082 and for several other streptomycetes. In addition, a blocked mutant of daptomycin producing GAL4111 was generated to prevent production of antibiotics in cultivations and designated as G011. Interestingly, all other cultivation properties of G011 were the same as found in GAL4111 except the lack of accumulation of lipopeptide antibiotics in detectable quantities in G011. G011 accumulates TAGs and the other lipids in similar quantities in the same cultivation conditions as GAL4111.

If referred to the standard methods in construction of genetically modified strains, these are found in the Streptomyces manual by Kieser et al., 2000 for streptomycetes and in Sambrook and Russell, 2001 for E. coli.

Plasmid Constructions:

The genes that are involved in fatty acid biosynthesis called sco0958 and sco5888 were cloned from S. coelicolor genomic DNA into pIJE486 vector to give pIJEsco0958 and pIJEsco5888, respectively. Using the same restriction sites the genes were cloned in a low-copy number vector pHJL401 to give pHJsco0958 and pIJEsco5888, respectively. Genes were also combined in same construct to give pIJEsco5888+0958 and pHJLsco0958+5888, respectively. The genes sco5888 and sco0958 were obtained by PCR using the homologous primers:

```
Sco5888for
                                           (SEQ ID NO: 7)
5' ATT TCTAGA AAA CCG TCC ATC ACG CGA G 3'
        XbaI Sco5888rev
                                           (SEQ ID NO: 8)
5' ATT AAGCTT ACTAGT ATG GTC GTC CTT GGT
TCA TC 3'
        HindIII SpeI
and Sco0958for
                                           (SEQ ID NO: 9)
5' ATT TCTAGA ACTAGT GAT CGT ACT TGA CCG
TAA TC 3'
        XbaI    SpeI Sco0958rev
                                           (SEQ ID NO: 10)
5' ATT AAGCTT GCTAGC CGA ACA GCG GAT TTT
ATT CAG 3'
        HindIII NheI
```

The fragments obtained by PCR were cloned into the vector pIJE486 using the corresponding restriction sites. For introduction of DNA into the strains GAL4111 and GAL1001, the protoplast transformation was used. A standard PEG-assisted transformation method was used. Transformation mixtures were plated on R2YE plates and incubated at 30° C. After overnight incubation 20 μg/ml thiostrepton in water suspension was spread on plates for the selection of plasmid containing strains. Incubation was continued for 3-5 days after which the transformants were picked up from the plates.

The fragments described above were ligated and cloned in E. coli by a standard procedure for transferring into Streptomyces species.

PCR products were verified by sequencing. Plasmids of the transformants were isolated and digested to verify transformed plasmid.

The following genetically modified strains were created and tested for increased accumulation of lipids as shown in Table 6.

TABLE 6

The designation of clones used in this invention.

| Code | Plasmid | Host strain |
| --- | --- | --- |
| G009 | pIJEsco0958 | GAL1001 |
| G010 | pIJEsco0958 | GAL4111 |
| G013 | pIJEsco5888 | GAL1001 |
| G014 | pIJEsco5888 | GAL4111 |
| G015 | pIJEsco5888 + 0958 | GAL4111 |
| G012 | pIJEsco0958 | G011 |
| G016 | pHJLsco5888 | GAL1001 |
| G017 | pHJLsco0958 + 5888 | GAL1001 |
| G019 | pHJLsco5888 | G011 | pIJE486 is a high copy number plasmid replicating in streptomycetes (Ylihonko et al., 1996)
pHJL401 is a low copy number plasmid replicating in streptomycetes (Kieser et al., 2000)

Example 3

Small-Scale Cultivation of GMO-Streptomycetes for Accumulation of Lipids

The strains G009, G010, G012, G013, G014, G015, G016, G017 and G019 were cultivated in the conditions as described here. The host strains, G011, GAL4111 and GAL1001 were used as controls in cultivations.

Typical Cultivation Conditions:
Temperature: 22-36° C.
pH: 5.0-8.5
agitation: 0-330 rpm
inoculum form: vegetative mycelia, substrate mycelia, spores
transferring rate: 0.5-50 G/0
medium in use: TSB, E05 as given in Example 1 and different kinds of waste or residue medias as described in example 4.

Figure 5:
FIG. 5 presents an example of the accumulation of TAGs in different media by the strains G017, G016, G013 and G011. Samples from left to right are GTM standard in concentrations of 40, 20, 10 and 5 g/l, samples of G017 after 0, 1, 2, and 5 day cultivation, samples of G016 after 2, 3, and 6 days cultivation, samples of G013 after 1, 2, 5 and 6 day cultivation, samples of G011 after 2, 3, and 6 day cultivation.

The accumulation of TAG was compared to that of the wild type, GAL1001 and GAL4111 by TLC analysis. FIG. 5 demonstrates an example of the accumulation of TAGs in different media by the strains G017, G016, G013 and G011. There was a clear increase in accumulation of lipids and especially TAGs in the GMO strains carrying the gene sco0958 and increase in those clones (strains) carrying sco5888 in different plasmid vectors. The results are given here:

TABLE 7

The designation of GMO strains used.

| Code | Cell mass (wet weight) % increase or decrease | TAG fraction by TLC (g/l) | Improvement-% of TAGs as compared to the parent. |
|---|---|---|---|
| G009 | −1% | 29 | 300 |
| G010 | −25% | 18 | 50 |
| G013 | −77% | 11 | 300 |
| G014 | +14% | 20 | 11 |
| G015 | +12% | 25 | 100 |
| G011 | +16% | 1 | 0 |
| G012 | −26% | 12 | 30 |
| G016 | −45% | 24 | 230 |
| G017 | +13% | 20 | 300 |
| G019 | +121% | 17 | 40 |

Example 4

Content of the Cultivation Broth: Usage of Waste for Growth

To enhance the maximum growth and accumulation of TAGs in economical, lowcost, cultivation conditions, several waste and/or fractions were used as carbon and/or nutrient sources in cultivations. Surprisingly, all the tested *streptomycetes* according to Example 1 and Example 2 were able to grow and accumulate lipids in a large spectrum of waste. The waste fractions were tested alone and with sugar, and in combination with other nutrients. The following waste fractions in Table 8 were successfully used as will be indicated by cell growth and accumulation of TAGs. The following data was derived from cultivations of G009 in the each non-hydrolysed (depolymerized) waste (50 g/l)+dextrose syrup (DX75) (10 g/l).

TABLE 8

The designation of materials mainly wastes or residues used in this invention as carbon and/or nutrient sources and their influence on growth and accumulation of TAGs.

| Material | Growth in CFU (CFU/ml) | Accumulation of lipids (% increase) as compared to cultivation In TSB |
|---|---|---|
| Bran and chaff | $10^4$ | +140 |
| Soya | $10^7$ | +100 |
| Corn steep liquor (CSL) | $10^6$ | +150 |

TABLE 8-continued

The designation of materials mainly wastes or residues used in this invention as carbon and/or nutrient sources and their influence on growth and accumulation of TAGs.

| Material | Growth in CFU (CFU/ml) | Accumulation of lipids (% increase) as compared to cultivation In TSB |
|---|---|---|
| Dextrose syrup | $10^6$ | NA |
| Starch syrup | NA | NA |
| Bacterial cell waste (lipids extracted) | $10^7$ | +94 |
| Molasses | $10^3$ | +120 |
| Mash | $10^4$ | +115 |
| Sludge | $10^3$ | +20 |
| OVR feed | <10 | NA |
| Farmamedia | $10^4$ | +120 |
| Bagasse | $10^2$ | NA |
| Straw | NA | +50 |
| Mink feed | NA | +10 |
| Offal | $10^3$ | +10 |
| Bone | $10^5$ | +20 |
| Organic waste (bio waste) vegetables | $10^7$ | +150 |
| Organic waste of garden | $10^4$ | +146 |
| Organic waste of bakery | $10^7$ | +139 |
| Algae biomass | $10^7$ | +203 |

* Estimated from 5 days sample-2 days sample

Example 5

Fermentations of the Selected Strains in the Controlled Conditions

The strains GAO 001, GAL4111, G009, and G010 were cultivated in the controlled fermentation conditions in the following range:
Temperature: 22-36
pH: 5.0-8.5
agitation: tip speed of 0-4 m/s
aeration: 0-2 vvm
inoculum form: vegetative mycelia, substrate mycelia, spores
passages: 0-2 seed
transferring rate: 0.5-50%
volume: 1.5 l working volume
Basic medium: TSB, 2*TY, E05 (the content of these media is given in Example 1, and several waste medias as shown in Table 9.

TABLE 9

Used waste or residue medias in fermentation.

CSL, 30 g/l; Dextrose syrup 10 g/l
CSL, 5-20 g/l; Meat 15-20 g/l
CSL, 5-20 g/l; Oat bran 15-20 g/l
CSL, 15 g/l; Dextrose syrup 10 g/l
CSL 30 g/l and Offal (class 2) 30 g/l
CSL, 10 g/l; Cell waste 50 g/l
CSL, 10 g/l; Dextrose syrup 10 g/l; Cell waste 50 g/l
Dextrose syrup 10 g/l; Cell waste 50 g/l
CSL 20 g/l, Soya 20 g/l, Dextrose syrup 10 g/l
Dextrose syrup 20 g/l, starch or straw or bagasse 20 g/l, bio waste 2.5-50 g/l, algae 50 g/l, $MgSO_4 \cdot 7H_2O$ 1 g/l, $KH_2PO_4$ 1 g/l, $CaCO_3$ 3 g/l Characters of the *Streptomyces culture:*
Time for exponential growth: 12-64 h
Time to accumulate lipids: 24-64 h
The main fraction of lipids based on TLC: TAGS The content of TAG in metabolite fraction as estimated by TLC: >8

The mass of chloroform extract: >15 g/l of culture broth

The TAG fraction of chloroform extract: 10-80%

Wet cell mass: >200 g/l

Dry cell mass: >20 g/l

The range of PMV %: 10-40

Increase of TAGs (highest amount−zero sample) by Image J: 4 g/l (time for highest value 6 days).

Example 6a

Batch Fermentation of the Strain G009

The said strain was cultivated at the fermentation volumes of 1.5, 20 and in 500 liter. The following procedure gives detailed information of the easily repeatable fermentation process.

Inoculation: spores or a plug of agar plate culture

Transferring rate: 4%

Seeding steps: 2

Temperature: 28° C.

Aeration: 0.5 vvm

Stirring: 100-280 rpm

Back pressure: 0.5 bar pH before sterilization: 7

Cycle time: 96 hours

Steady state reached: 24 hours (DO is 0 after 24 hour cultivation)

Cultivation medium: several waste and/or residue medias as given in Example 5, E05, the ingredients of the basic E05-medium is given here and the materials that can be used to replace them (Table 10).

TABLE 10

The ingredients that are used to replace basic E05-medium materials

| Ingredient | Replaceable | g/l |
|---|---|---|
| dextrose | Syrup (5-20 g/l) | 20.00 |
| starch | Bagasse or straw | 20.00 |
| farmamedia | Bio waste* (2.5-50 g/l), | 5.00 |
| yeast extract | algae debris** (2.5-100 g/l), bacterial cell debris*** (50-200 g/l) | 2.50 |
| $MgSO_4 \cdot 7H_2O$ | Essential | 1.00 |
| $KH_2PO_4$ | Not essential | 1.00 |
| $CaCO_3$ | Not essential | 3.00 |
| NaCl | Not essential | 3.00 |

*= compostable waste like domestic, bakery, garden, vegetables, brewery (e.g. mash), offal or mixture of these; composition varies
**= *Phaeodactylum*, *Chlorella* and *Dunaliella*
***= any cell mass, e.g. lactobacilli and streptomycetes Cell mass (wet): 348 g/l

PMV: 30%

Chloroform extract dried: 28 g/l

TAGs obtained based on TLC: 23 g/l

TAGs in chloroform extract: 82%

Ratio to convert fed sugar to TAGs: from 40 g/l to 23 g/l 57.5% (additional sugar from waste) (the yield was calculated based on pure sugar (dextrose and starch) added only). Theoretical maximum is 33%. Yield higher than theoretical maximum means that lipids are produced from sugars included in waste materials. Increase of TAGs (highest amount−zero sample) by Image J: 10.2 g/l (time for highest value 6 days)

Example 6b

Batch Fermentation of the Strain GAL1001

The said strain was cultivated at the fermentation volumes of 1.5 l, 20 l and in 500 l. The explained procedure given in example 6a gives detailed information of the easily repeatable fermentation process.

The Indicative Figures of Cultivations:

Cell mass (wet): 267 g/l

PMV: 25%

Chloroform extract dried: 10 g/l

TAGs obtained: 5 g/l

Ratio to convert fed sugar to TAGs: from 40 g/l to 5 g/l=12.5%

Increase of TAGs (highest amount−zero sample) by image J: 2.1 g/l (time for highest value 3 days).

Example 7

Fed-Batch Fermentation of the Strain G009

The said strain was cultivated at the fermentation volumes of 1.5, 20 and in 500 liter. Parameters as described in Example 6a. Feeding of dextrose start after 1-2 days of cultivation, when primary glucose was mostly consumed, and was continued to the end of cultivation. The amount of fed sugar is 40 g/l as a total so total amount of sugar added to culture broth was 60 g/l.

The Results Per One Liter of the Culture Broth Obtained in 4-Days Fermentations:

Cell mass (wet): 356 g/l

PMV: 36%

Chloroform extract dried: 1.4 g/l

TAGs obtained: 6 g/l

Ratio to convert fed sugar to TAGs: from 60 g/l to 6 g/l=10% Increase of TAGs (highest amount zero sample) by Image J: 3.6 g/l (time for highest value 3 days)

The examples indicates that fed-batch cultivation can be used in the lipid production by *Streptomyces*.

Example 8

Combination of Different Waste in Broth; Algae and Biowaste

The strain G009 was cultivated in the controlled conditions in a broth made by combining different type of waste and in the following parameters:

Temperature: 28° C.

pH: 7 in the beginning of cultivation agitation: 300 rpm aeration: 0.5 vvm inoculum form: vegetative mycelia, substrate mycelia, spores passages: 2 transferring rate: 2% volume: 1.5 L working volume

TABLE 11

Used wastes and/or residues in fermentation.

biowaste (bakery&vegetables (50:50), content not defined; 10 g/l
algae (*Dunaliella*) 50 g/l
main sugar source: bagasse
sugar (total) 40 g/l (dextrose syrup and starch/bagasse/straw)

Figure 4:
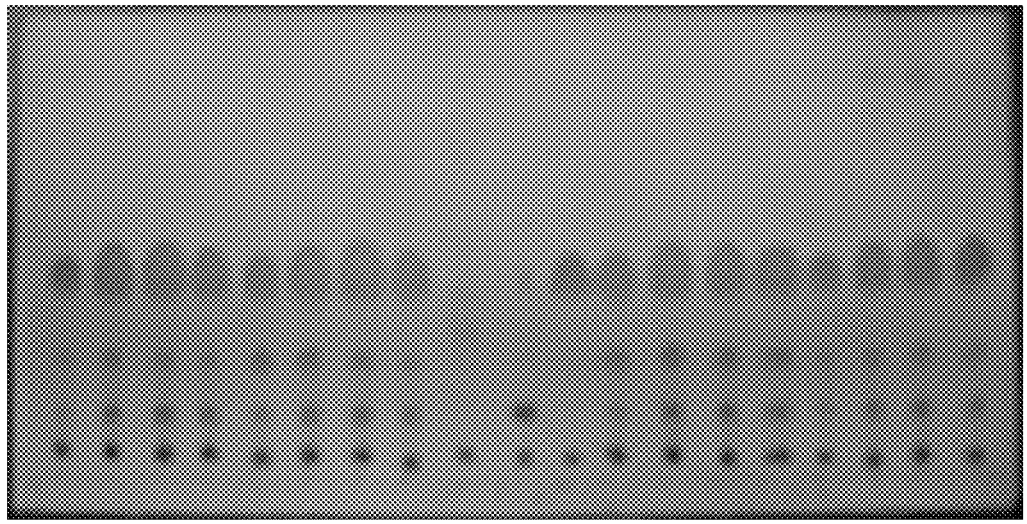
FIG. 4 presents an example of the accumulation of TAGs in different media by G009. Samples from left to right are E05-14 medium after 0, 2, 5 and 7 days, E05-15 medium after 0, 2, 5, and 7 day cultivation, standards COD (Cholesterol octadecanat), C (Cholesterol) and GTM (Glyceryl trimyristate), E05-16 medium after 0, 2, 5 and 7 day, E05-17 medium after 0, 2, 5 and 7 day cultivation.

Characters of G009 Culture:
Time for exponential growth: 97 h
Time to accumulate lipids: 144 h
The main fraction of lipids: TAGs
The content of TAG in metabolite fraction as estimated by TLC: >70% % FIG. 4 demonstrates the accumulation of TAGs in different media by G009.
The mass of chloroform extract: >22 g/l of culture broth The TAG fraction of chloroform extract 68.9%
TAGs as determined by ImageJ: 15.3 g/l
PMV: 39%
Lipid yield (total fed pure sugar without waste): 55%
Increase of TAGs (highest amount–zero sample) by Image J: 4.6 g/l (time for highest value 3 days)

The example indicates that various wastes and residues can be provided as mixes in the lipid production by *Streptomyces*. Lipid yield exceeded theoretical value of 33% indicating that sugars are used from waste.

Example 9

Reuse of Lipid-Extracted Bacterial Cultures as Nutrient Source in Fermentation

The strains G016, G013 and G009 were cultivated in the controlled conditions in 1.5 liter batch fermentation. The cells were harvested by filtration and extracted by the equal volume of chloroform (1:1). After that the remaining cell debris was further dried to remove chloroform residuals at 60° C. for 10 min to be supplied to fermentation medium with or without additional sugar sources, such as dextrose syrup 10 g/l.
Temperature: 22-36° C.
pH: 5.0-8.5
agitation: tip speed of 0-4 m/s
aeration: 0-2 vvm
inoculum form: vegetative mycelia, substrate mycelia, spores
passages: 0-2 seed
transferring rate: 0.5-50%
volume: 0.05-1.5 l working volume
Characters of G016 Culture:
Time for exponential growth: 20-144 h
PMV: 33%
Time to accumulate lipids: until 72 hours
The main fraction of lipids: TAGs
The content of TAG in metabolite fraction as estimated by TLC: >80%
The mass of chloroform extract: 27.4 g/l
TAGs calculated from quantity in chloroform extract: 14 g/l
Lipid yield (from total sugar without waste): 51%
Increase of TAGs (highest amount–zero sample) by Image J: 1.6 g/l (time for highest value 3 days)
Characters of G013 Culture:
Time for exponential growth: 20-144 h
PMV: 33%
Time to accumulate lipids: until 144 hours
The main fraction of lipids: TAGs
The content of TAG in metabolite fraction as estimated by TLC: >80%
The mass of chloroform extract: 20.5 g/l
TAGs calculated from quantity in chloroform extract: 10 g/l
Lipid yield (from total sugar without waste): 49%
Increase of TAGs (highest amount–zero sample) by Image J: 2.6 g/l (time for highest value. 3 days)
Characters of G009 Culture:
Time for exponential growth: 6-50 h
PMV: 20%
Time to accumulate lipids: until 48 hours
The main fraction of lipids: TAGS
The content of TAG n metabolite fraction as estimated by TLC: >90%
The mass of chloroform extract: 14 g/l
TAGs calculated from quantity in chloroform extract: 7.0 g/l
Lipid yield (from total sugar without waste): 50%
Increase of TAGs (highest amount–zero sample) by Image J: 3 g/l (time for highest value 3 days)

The example indicates that lipid extracted *Streptomyces* cells can be re-used as a nutrient source in lipid production by *Streptomyces*.

Example 10

Pasteurize Ion of Media

In parallel with the typical fermentation scheme, the cultivation without sterilization of the used broths was carried out. The sterilization at 121° C. for 20 minutes was replaced by warming up to 60° C. 10-30 min and 75° C. for 2-10 minutes of both seed and production broths. The cultures were daily studied by microscopy and by plating a sample of 100 µl on ISA (Tryptone Soya agar) plates allowing the growth of a large spectrum of microbes. Typically no contaminations were found in the cultures even with shortest heating time and the cultivations were similar to parallel cultivations in sterile media.
Inoculation: Spores or a Plug of Agar Plate Culture
Transferring rate: 4%
Seeding steps: 2
Temperature: 28° C.
Aeration: 1 vvm
Stirring: tip-speed 1.3 m/s
Back pressure: 0.5 bar
pH before sterilization: 7
Cycle time: 96 hours
Steady state reached: 16 hours
Cultivation medium: several waste medias as given in Example 5, E05, 20 g/l offal+20 g/l dextrose syrup.
Results:
Cell mass (wet): 178 g/l
PMV: 16%
Time to accumulate lipids: until 72 hours
The mass of chloroform extract: 9 g/l
TAGs obtained (estimated by TLC): 5 g/l
Time to accumulate lipids: until 96 hours
The main fraction of lipids: TAGs
The content of TAG in metabolite fraction as estimated by TLC: >90%
Increase of TAGs (highest amount–zero sample) by Image J: 1.8 g/l (time for highest value 6 days)

The results indicate that the sterilization of medium can be replaced by medium pasteurization for lipid production by *Streptomyces*.

Example 11

Determination of the Cell Growth for Lysis

In the cultivation conditions described in Examples 1-7 above, the steady state was typically reached in 10-48 hours incubation. The stationary stage continues for about 48-72 hours after which the cell lysis took place. TAGs disappear at prolonged cultivation. Only minor quantities of TAGs—if any—were detectable on TLC in samples derived from 7-days culture broths. The lipids and especially TAGs decreased gradually already on the 4$^{th}$ cultivation day as was detected by TLC. Cell lysis may have liberated the action of lipases resulting in hydrolysis of TAGs as was seen in the cultivation experiments. Therefore, the fermentation was stopped before autolysis or an inhibitor of lipases was added to the culture broth.

Example 12

Prevention of TAG Degradation

The spores of the strain G009 were cultivated in the medium containing the following raw materials in 1 L of tap water, pH 7: Dextrose 75 20 g, Bagasse 20 g, Biowaste from bakery and garden (1:1) 5 or 10 g, Algae 25 to 50 g, MgSO$_4$.7 H$_2$O 1 g, KH$_2$PO$_4$ 1 g and CaCO$_3$ 3 g. The cultivation conditions were 28° C., 300 rpm for 11 days. After 6 days of cultivations, 0.05 g/l AgNO$_3$ or 0.4% of TritonX100 solution containing 0.05 g/l of CaCO$_3$. The flasks without the said supplements were considered as controls for lipase inhibition treatment study. Cultivation was continued in the same conditions for 5 days more.

The samples were taken after 7, 8 and 11 days of cultivations according to the general sampling protocols used in this invention and the results of sampling are shown here. The parallel cultivations were done with two concentrations of both algae debris and biowaste and the upper row of each test condition gave a result with higher concentration of both waste fractions.

TABLE 10

The results of lipase inhibition test

| The supplements | Weight of Chloroform extract (g/l) | | Quantity of TAGs g/l by Image J | | |
|---|---|---|---|---|---|
| | 7 day | 11 day | 7 day | 8 day | 11 day |
| No; control | 7.6 | 6.1 | 5 | 4.9 | 0.5 |
| AgNO$_3$ | 7.7 | 8.5 | 4.8 | 4.8 | 4.8 |
| TritonX100 + CaCO$_3$ | 10.3 | 10.1 | 5 | 5 | 4.9 |

The effect of lipase inhibitors was very well seen in the mass of lipids (chloroform extract) which was slightly increasing or stabile. The remarkable difference in changes of quantity of TAGs as compared to control was noticed.

Example 13

Generation of Non-Producing Mutants by Random Methods Using a Chemical Mutagen

There are several possibilities to generate blocked mutants from an antibiotic producer strain. In this example strain *S. milbemycinius* GAL4211, producing an anti-biotic called Milbemycin was used for NTG mutagenesis. The strain was plated on thick ISP4 agar plate (9 cm) and incubated at 30° C. until spores were formed. The spores were suspended to 10 ml water and transferred to centrifuge tube for shaking smoothly. A homologous suspension of spores was filtered through a 3 cm cotton wool and centrifuged 3000 rpm, 10 min. The harvested spores were stored in 20% glycerol at −80° C. and the spore titre was determined by plating suitable dilutions on agar plates for colony counting.

The spore suspension with the content of 10$^7$ spores 1 ml was treated by NTG, (N-methyl-N'-nitro-N-nitrosoguanidine) at different concentration of 1-3 mg/ml in pH buffers of 7-9 at +30° C. for 0.5-1 h. After NTG-treatment, the cells were washed twice and plated on ISP4 plates. Killing rates observed in the said conditions were 90-100%.

The colonies failed to produce antibiotics as was tested by antibacterial assay and by HPLC (240 and 430 nm) analysis were studied for accumulation of lipids.

Example 14

Generation of Non-Producing Mutants by Targeted Inactivating of the First Biosynthetic Genes The polyketide biosynthesis (PKS) genes were cloned by PCR using heterologous but conservative DNA fragment. The fragment was isolated and cloned into a vector pUC19 replicating in *E. coli* but not in *streptomycetes*. A biomarker, a gene encoding apramycin resistance was inserted in the PKS gene to cause a truncation of the gene product. The recombinant pUC19 construct obtained was introduced into *S. milbemycinius* by conjugation. The clones were studied for expression of antibacterial properties and analyzed for production of milbemycins by HPLC. The verification for non-producing of characteristic antibiotic, milbemycins was done by repeated cultivations in liquid medium and on solid agar.

```
Primers used:
                                         (SEQ ID NO: 11)
    forward:      5' TSGCSTGCTTGCTTCGAYGCSATC-3'

(SEQ ID NO: 12)
    reverse:      5' TGGAANCCGCCGAABCCGCT-3'
```

Degenerated primer symbols: S=C or G; Y=C or T; B=C, G or T and N=A, T, C or G.

PCR Conditions:

| Cycle step | Temperature | Time | Number of cycles |
|---|---|---|---|
| Initial denaturation | 98° C. | 3 min | 1 |
| Denaturation | 98° C. | 30 s | 30 |
| Annealing | 60° C. | 30 s | |
| Extension | 72° C. | 30 s | |
| Final extension | 72° C. | 10 min | 1 |

Conjugation:

For conjugation the recombinant pUC19 construct were transformed into Emil strain ET12567/pUZ8002. A colony was inoculated into 3 ml LB or 2×TY containing kan, cam and apr and grown overnight at 30° C., 330 rpm. Overnight culture was diluted 1:30 in fresh LB or 2×TY containing antibiotics and grown at 30° C. to an OD$_{600}$ of 0.4-0.6. Cells were washed twice with an equal volume of media and re-suspended to 0.1 volume of used media. 1 ml of spore suspension of *S. milbemycinius* with the content of 10$^7$ spores/ml was washed twice with an equal volume of TSB and re-suspended to 1 ml of TSB. 100 μl or 250 μl of spore suspension was added 400 μl or 250 μl *E. coli* suspension and mixed. 100 μl of suspension was plated on four MS+10 mM $MgCl_2$ plates and incubated at 30° C. 16-20 h. Conjugants were selected by resistance against an antibiotic (apramycin 50 mg/l) and nalidixic acid (1 mg/plate) was used to kill *E. coli*. Antibiotics were suspended in sterile purified water and overlaid on plates.

Example 15

A Blocked Mutant Derived from the Strain *Streptomyces milbemycenius* and Accumulating Enhanced Quantities of Lipids The mutant was cultivated in the medium E05. The strain was cultivated at 28° C., 200 rpm in flasks and in a fermentor of 200 L working volume using aeration of 0.5 vvm, agitation 250 rpm and at 28° C. One seed cultivation was made to enhance cell mass for 200-l cultivation with the inoculation rate of 10%. After eight days cultivation either in flask or fermentor, the whole culture broth obtained was extracted with methanol:chloroform (2:8) for 2 h at RT by shaking. The chloroform phase containing lipid fraction was studied by TLC for the amount of lipids and 20 g/l as the minimum was detected. The efficiency of conversion of pure glucose or glucose (20 g/l) derived from starch (40 g/l) is 33%. The amount of TAGs was in the range of 80-90% of all lipids. The cell mass was relatively low giving a low PMV value of 10-20% in the end of cultivation.

GC analysis revealed that the lipid profile was characteristic to *Streptomyces* strain.

Example 15

Characterizations of the GMO-Strains

The strain characterization was carried out by the studies on colony morphology, cycle time and production of metabolites.

PCR products used to construct GMO strains were verified by sequencing. Plasmids of the strains were isolated and digested to verify transformed plasmids.

The strains characters on ISP4 and ISP2 agar plates and in submerged cultivations in TSB and in E05 with waste variants are given here.

G009 is a *Streptomyces albus* GAL1001 strain carrying pIJEsco0958 and designated as clone 2. It does not produce detectable quantities of bioactive metabolites and like GAL1001 it is suggested to be blocked in biosynthesis of bioactive secondary metabolites due to a random mutation. Colony morphology: On ISP4 agar G009 form spores with white pigment while in the reverse side of agar plate; the colonies are brown surrounding by a thin bright zone. In a rich agar, ISP2, G009 colonies form yellow substrate mycelia and yellowish aerial hyphae. Spores of white pigment are slightly visible. Typical morphology in submerged culture is pellet or dispersed mycelia. The strain forms spores also in submerged cultivations e.g. in TSB and in E05. The relevant characters according to this disclosure are increased cell mass as compared to the parent strain and accumulation of TAGs in a variety of cultivation condition up to 30 g/l. The characters of the strain are stabile in passages up to 20 times tested so far.

G013 is a *Streptomyces albus* GAL1001 strain carrying pIJEsco5888. It does not produce detectable quantities of bioactive metabolites and like GAL1001 it is suggested to be blocked in biosynthesis of bioactive secondary metabolites due to a random mutation. Colony morphology on solid—and submerged cultivations is very similar to that described for G009 though the growth is not as good as found by G009. The colony size is somewhat smaller than found in G009 cultures on solid agar. The relevant character according to this disclosure is accumulation of TAGs in a variety of cultivation condition up to 11 g/l.

G016 is a *Streptomyces albus* GAL1001 strain carrying pHJLsco5888. It does not produce detectable quantities of bioactive metabolites and like GAL1001 it is suggested to be blocked in biosynthesis of bioactive secondary metabolites due to a random mutation. Colony morphology on solid and submerged cultivations is very similar to that described for G009 though the growth is not as good as found by G009 but slightly better than found by G013. The relevant character according to this disclosure is accumulation of TAGs in a variety of cultivation condition up to 24 g/l.

G011 is a mutant of GAL4111 and does not produce detectable quantities of bioactive metabolites characteristic to its parent strain. GAL4111 has been identified to be *Streptomyces roseosporus* based on identical patterns of DNA sequence, colony characteristics and ability to produce small quantities, some milligrams per liter of Daptomycin analogues. Colony morphology: On ISP4 agar G011 form spores with white/red pigment while in the reverse side of agar plate, the substrate mycelia is from reddish to brown and a thin clear zone around these red/brown colonies is visible indicating an amylase activity. In a rich agar, ISP2, G011 colonies are brown, slight sporulation with white/red pigment is seen. The substrate mycelia on ISP2 are slightly red with brownish aerial hyphae. In submerged cultivations it provides reddish pellet or dispersed mycelia. The strain forms spores also in submerged cultivations e.g. in TSB and in E05. The relevant characters according to this disclosure are increased cell mass as compared to the parent strain and accumulation of TAGs 1 g/l.

G012 is a *Streptomyces roseosporus* G011 strain carrying pIJEsco0958 and does not produce detectable quantities of bioactive metabolites like its parent strain G011. Colony morphology is identical to that described for G011. The growth is not, however, as good as found by G011. The colony size is somewhat smaller than found in G011 cultures on solid agar while the colonies could be not distinguished based on that. The relevant character according to this disclosure is accumulation of TAGs 12 g/l.

G017 is a *Streptomyces roseosporus* G011 strain carrying pHJLsco0958+5888 and does not produce detectable quantities of bioactive metabolites like its parent strain G011. Colony morphology is identical to that described for G011. The growth is very similar to that found by G011, The relevant characters according to this disclosure are increased cell mass as compared to the parent strain and accumulation of TAGs 20 g/l.

G019 is a *Streptomyces roseosporus* G011 strain carrying pHJLsco5888 and does not produce detectable quantities of bioactive metabolites similar to its parent strain G011. Colony morphology is identical to that described for G011. The growth is very similar to that found by G011. The relevant characters according to this disclosure are increased cell mass as compared to the control strain GAL4111 and accumulation of TAGs 17 g/l.

3010 is a *Streptomyces roseosporus* GAL4111 strain carrying pIJEsco0958 and does not produce detectable quantities of bioactive metabolites dissimilar to its parent strain GAL4111. Colony morphology is identical to that described for G011. The growth is not, however, as good as found by G011. The relevant character according to this disclosure is accumulation of TAGs 18 g/l.

G014 is a *Streptomyces roseosporus* GAL4111 strain carrying pIJEsco5888 and does not produce detectable quantities of bioactive metabolites dissimilar to its parent strain GAL4111. Colony morphology is identical to that described for G011. The growth is very similar to that found by G011. The relevant characters according to this disclosure are increased cell mass as compared to the parent strain GAL4111 and accumulation of TAGs 20 g/l like G017.

G015 is a *Streptomyces roseosporus* GAL4111 strain carrying pIJEsco5888+0958 and does not produce detectable quantities of bioactive metabolites dissimilar to its parent strain GAL4111. Colony morphology is identical to that described for G011. The growth rate is very similar to that found by G011. The relevant characters according to this disclosure are increased cell mass as compared to the parent strain GAL4111 and accumulation of TAGs 25 g/l.

LIST OF REFERENCES

Alvarez, H. M., Steinbüchel A. (2002) Triacylglycerols in Prokaryotic microorganisms. Appl Microbiol Biotechnol 60: 367-376.

Arabolaza, A, Rodriguez, E, Altabe, S, Alvarez, H and Gramajo, H (2008) Multiple pathways for triacylglyserol biosynthesis in *Streptomyces coelicolor*. Appl Env Microb 79: 2573-2582.

Běhal, V, Jilek, M. (1969) Regulation of biosynthesis of secondary metabolites. VII. Dynamics of fatty acid content during fermentation in *Streptomyces aureofaciens*. Folia Microbiol (Praha) 14:211-4.

Campbell, M. N. (2008) Algae as a Renewable Source for Liquid Fuel; Biodiesel: Algae as a Renewable Source for Liquid Fuel. Guelph Engineering Journal, (1), 2-7. 1916-1107.

Coen, D. M. 2001 The polymerase chain reaction, published in Ausubel F M, Brent R, Kingston R E, More D D, Seidman J G, Smith K. and Struhl K (eds.) Current protocols in molecular biology. John Wiley & Sons. Inc., Hoboken, USA).

Cole, A, Shareck, F. (2008), Cloning, purification and characterization of two lipases from *Streptomyces coelicolor* A3(2), Enzyme and microbial technology 42: 381-388.

Gellissen, G., (ed), (2005). Production of recombinant proteins. Novel microbial and eukaryotic expression systems. Wiley-VCH Verlag GmbH & Co. Weinheim, Germany.

Gesheva, V., Rachev, R., Bojkova, S. (1997) Fatty acid composition of *Streptomyces hygroscopicus* strains producing antibiotics Lett Appi Microbiol 24: 109-112.

Gräfe, U., Reinhardt, G., Hänel, F., Schade, W., Gumpert, J. (1985). Occurrence or squalene and dehydrosqualene in streptomycets. J. Basic Microbial. 25(8):503-507

Gunstone, F. D., Harwood, J. L., Dijkstra, A. J. (ads) (2007) The lipid handbook, 3rd edn. CRC Press, Boca Raton.

Kaddor, C., Biermann, K., Kalscheuer, R., Steinbüchel, A I. (2009) Analysis of neutral lipid biosynthesis in *Streptomyces avermitilis* MA-4680 and characterization of an acyltransferase involved herein. *Applied Microbiology and Biotechnology*, Volume 84, Number 1, August 2009, pp. 143-155.

Kieser, T., Bibb, M. J., Buttner, M. J., Chater, K. F., Hopwood, D. A. (2000) Growth and preservation of *Streptomyces*. In Practical *Streptomyces* genetics, The John Innes Foundation.

Le, S. Y., Lee, B. H. (2006). Esterolytic and Lipolytic Activities of *Lactobacillus Casei*-subsp-*Casei* LLG. Journal of Food Science 55: 119-122.

Li, Y., Florova, G., Reynolds, A. (2005). Alteration of the fatty acid profile of Streptomyces coelicolor by replacement of the initiation enzyme 3-ketoacyl acyl carrier protein synthase III (FabH). J Bacteriology 187: 3795-3799.

Meng, X., Yang, J., Xu, X., Zhang, L, Nie, Q., Xian, M. (2009). Biodiesel production from oleaginous microorganisms, Renew. Energ. 34:1-5.

Nagao, A, Ishida, N. and Terao, J. (1991) Synthesis of 6-phosphatidyl-L-ascorbic acid by phospholipase D. Lipids 26: 390-394.

Novak, J., Hájek, P., Rezanka, T., and Veněa, Z. (1992) Nitrogen regulation of fatty acids and avermectins biosynthesis in *Streptomyces avermitilis*. FEMS Microbiol Lett.72(1): 57-61.

Olukoshi, E. R., Packter, N. M. (1994). Importance of stored triacylglycerols in *Streptomyces*: possible carbon source for antibiotics. Microbiology 140:931-943

Packter, N. M. and Olukoshi, E. R. (1995) Ultrastructural studies of neutral lipid localisation in *Streptomyces*. Arch Microbial 164: 420-427.

Ratledge, C., Cohen, Z. 2008. Microbial and algal oils: Do they have a future for biodiesel or as commodity oils. Lipid Technology 20:155-160.

Ratledge, C., Seekstra, H., Cohen, Z., Fichteli, J. 2005. Down-stream processing, extraction, and purification of single cell oils. In Single Cell Oils. Cohen Z, Ratledge C (eds). AOCS Press, Champaign, Ill., U.S. 202-219.

Rice, P., Longden, I. and Bleasby, A. (2000) EMBOSS: the European Molecular Biology Open Software Suite, Trends Genet, 16, 276-277.

Soror, S. H., Verma, V., Rao, R., Rasool, S., Koul, S., Qazi, G. N., Cullum J. 2007. A cold-active esterase of *Streptomyces coelicolor* A3(2): from genome sequence to enzyme activity Journal of Industrial Microbiology and Biotechnology 34: 525-531, Strobel, G. A., Knighton, B. Kluck, K., Ren, Y., Livinghouse, T. Griffin M., Spakowicz, D. and Sears, J. (2008) The production of myco-diesel hydrocarbons and their derivatives by the endophytic fungus *Gliocladium roseum* (NRRL 50072). Microbiology 154 (2008), 3319-3328; DOI 10.1099/mic.0.20081022186-0.

Suutari, M. and Laakso, S. (1992) Changes in fatty acid branching and unsaturation of *Streptomyces griseus* and *Brevibacterium fermentans* as a response to growth temperature. Appl Env Microb 58: 2338-2340.

Wälternann, M., Stöveken, T and Steinbüchel. A. (2007). Key enzymes for biosynthesis of neutral lipid storage compounds in prokaryotes: Properties, function and occurrence of wax ester synthases/acyl-CoA:diacylglycerol acyltransferases. Biochimie 89: 230-242.

Ylihonko, K, Tuikkanen, J, Jussila, S, Gong, L and Mäntsälä, P (1996) A gene cluster involved in nogalamycin biosynthesis from *Streptomyces nogalater*: sequence analysis and complementation of early-block mutations in the anthracycline pathway. Mol Gen Genet. 251:113-120.

The invention claimed is:

1. A process for producing triacylglycerols, which comprises
cultivating bacterial cells of the genus *Streptomyces* in a medium comprising organic waste(s) or residue(s) or mixtures thereof as carbon and/or nutrient source(s), wherein the organic waste(s) or residue(s) comprise lignocellulosic waste(s) or lignocellulosic residue(s);
recovering the triacylglycerols from the cells or from the culture medium, wherein the amount of triacylglycerols produced in the culture medium is at least 5 g/liter.

2. The process according to claim 1, wherein the organic waste(s) or residue(s) or mixtures thereof are the main source(s) of carbon and/or nutrient(s) in the cultivation medium.

3. The process according to claim 1, wherein the organic waste(s) or residue(s) comprise(s) industrial organic waste(s) or residue(s), agricultural organic waste(s) or residue(s), municipal waste(s) or microbial waste(s) or residue(s), or any mixtures thereof.

4. The process according to claim 1, wherein the cultivation medium comprises as an additional carbon source glycerol, a fraction from sugar or starch industry, sugar or starch syrup(s) or purified sugar(s) or any mixtures thereof.

5. The process according to claim 1, wherein the produced triacylglycerols are transesterified to produce biodiesel or hydrogen treated to produce renewable diesel.

6. The process according to claim 1, wherein the cultivation medium is not sterilized or is pasteurized.

7. The process according to claim 1, wherein the cultivation medium comprises lipase inhibitors.

8. The process according to claim 1, wherein the cultivation is carried out as a batch or as a fed-batch fermentation.

9. The process according to claim 1, wherein the *Streptomyces* species is selected from the group of *Streptomyces roseosporus, Streptomyces griseus, Streptomyces albus, Streptomyces peucetius, Streptomyces aureofaciens, Streptomyces lividans, Streptomyces coelicolor, Streptomyces hygroscopicus, Streptomyces avermitilis, Streptomyces milbemycinius* and *Streptomyces lydicus*.

10. The process according to claim 1, wherein the *Streptomyces* host is genetically modified to express an endogenous or exogenous gene encoding diacylglycerol acyltransferase (DGAT) (EC 2.3.1.20) and/or 3-ketoacyl-acyl carrier protein synthase III (FabH) (EC: 2.3.1.41).

11. The process according to claim 1, wherein the *Streptomyces*, host is genetically modified to express one or more of genes selected from the group of
(a) *Streptomyces* coelicolor gene 0985 (sco0958) of SEQ ID NO: 1; and/or *Streptomyces coelicolor gene* 5888 (sco5888) of SEQ ID NO:2; and
(b) a nucleotide sequence encoding an amino acid sequence showing at least 85% identity to SEQ ID NO: 3 and having DGAT activity, or a nucleotide sequence encoding an amino acid sequence showing at least 85% identity to SEQ ID NO: 4 and having FabH activity.

12. The process according to claim 1, wherein the *Streptomyces* host is made deficient in producing bioactive metabolites.

13. The process according to claim 12, wherein the bioactive metabolites, comprise antibiotic agents.

* * * * *

SEQUENCE LISTING

<160> NUMBER OF SEQ ID NOS: 12

<210> SEQ ID NO 1
<211> LENGTH: 1860
<212> TYPE: DNA
<213> ORGANISM: Streptomyces coelicolor
<220> FEATURE:
<221> NAME/KEY: gene
<222> LOCATION: (1)..(1860)

<400> SEQUENCE: 1

| | | | | | |
|---|---|---|---|---|---|
| gtgcggtaga | tgtgcgaggt | ggcccggcgg | accgcgatcg | cgtcggggtg | gtcgacgtcc | 60 |
| agctcgtcga | gttccttcag | tacgtcgagg | cagagcgcca | gccgttcggg | gtcgataccg | 120 |
| gggccgtacg | cggacgccgc | cacctcgtcc | gtggtcgccg | caccgtcctg | tgtcaccgtc | 180 |
| atcgccgctg | ccgttccctg | gtcaccgtcg | cggcgctccg | ggaggcgacc | gctgtcgaac | 240 |
| agcggatttt | attcagcgcg | cggcgtggat | ccaaacccgc | cggggtcagg | acggcacgc | 300 |
| cgtgagcaac | gtctccacct | cctcggccac | cgccacggcg | agccggtcga | ggtccggcac | 360 |
| cgccttcgcg | tcggcgagca | ggccgtagtg | gacccgcccg | cggtacgtcg | agacggccac | 420 |
| cgccagggag | tggccgcggg | ccagcggggc | cagtggatag | acctcggtga | gcgggtgccc | 480 |
| gcccagccgc | agcccgaggc | tgggcagggg | gacgctggtg | accaggaggt | cgaaccagag | 540 |
| ccgggcggcc | ccggagacca | gtggcccgcc | gagccggtgg | ccgagcgccg | ggacgtggtc | 600 |
| ggcgagcagg | gcgacggctc | cggcgccgcg | tccgggcccg | cgtccttgt | tgcggtccat | 660 |
| ggcggcgcgg | accgtgccga | ggcgggcgag | cgggtcgggg | tcgccgaccg | gaagcctcat | 720 |
| caggtacccg | gagagccggt | ttccctgggg | gtgcgcgctg | cgcgggcggc | gcctggagac | 780 |
| ggggatcagg | gcccggggcg | cgacgccctc | gctgccgtcg | ccgcgttcgt | ccagccagcg | 840 |
| gcgcagggcg | cccgcgacga | ccgcgatcag | tacgtcgttg | acggtgccgc | cggtggtctt | 900 |
| gcggacgtgg | tgcacgtcgt | cgaggtcgac | ggacaccccc | gcggtccggc | gggtcccgga | 960 |
| ggacgcggcg | gtgagcgcgg | gcgaggaacg | cacgtcgagg | gtggacaacg | ccgcggcggc | 1020 |
| accgatgtcc | agggcgcgcc | cggcgtcgga | cagggcgccg | cgcagccggt | cgggcagggc | 1080 |
| gcgcacgtcc | ggcaggagtc | cgcgcggcgg | ctgctcgggg | cggggccggg | gtgccggcag | 1140 |
| gtccatcggg | tccaggacac | ccgcggccag | cgtcagggcg | cgcagaccgt | cggccagggc | 1200 |
| gtggtggaac | ttgaacagca | cggcgaagga | cccgccgtcc | gcgcccggca | gcacgtgcgc | 1260 |
| ctcccacggc | ggccgtccgc | gttccagggg | gcgttccatc | aggcgcccgg | cccgggcgtg | 1320 |
| gaagtccgtg | gccggggcgt | gcagccgcac | gtggtcgagc | gggtcgaagc | ggggtcggg | 1380 |
| ctcgcgggtc | gcgccgccga | acgcgaacgg | ccggcgcagg | gccatcggcg | gctgccaggt | 1440 |
| gtcccggatc | ctcatccgca | gtccgggcac | cgcgggggcg | cgggccgcga | gcaggtccgc | 1500 |
| cgcgagcgcg | cccgcggtgg | gcgagtcggc | ctcgaagacg | ccgagcgcgc | ccaggtgcat | 1560 |
| ggggtgctcg | gcggactcga | tgttccagaa | cgccaggtcg | aggggagcga | gcggatcggg | 1620 |
| agtcaagggc | ttgcctcgca | aggacgacgc | atgggcggtg | gatggacaac | gggtggacaa | 1680 |
| gcagtcaatc | gctctccgac | gattacggtc | aagtacgatc | acgctacgca | cagttaacaa | 1740 |
| gagattaaaa | gtcccgcccc | tttcgacagg | ggcgggactg | ctgtgactca | tggggcgcct | 1800 |
| gtgctcgcgt | cggctcaggt | cagcggcggc | ggcaccgcct | ctgtcccggt | accccacccg | 1860 |

<210> SEQ ID NO 2
<211> LENGTH: 1380

```
<212> TYPE: DNA
<213> ORGANISM: Streptomyces coelicolor
<220> FEATURE:
<221> NAME/KEY: gene
<222> LOCATION: (1)..(1380)

<400> SEQUENCE: 2
cagtgagccg tcagcgcccg gtcagggggcc ccggccagac tcggtgcggc cgggggggccc      60 ggattcactc cccacacctg ccggccggca aaccgtccat cacgcgagga gcacacacgt     120
ggtttcccgt ctccgccgcc gcaccaggcc caccgcacac cgcggccgct ccgcgggcgg     180
tgcccggtga cccgggcgtc cgtgctgacc ggcctcggtt cctgtctgcc gtcccggtgc     240
gtcaccaacg cggagctgga gcggacgatg gacacctcgg acgagtggat ccgggcccgt     300
acggggatcg cccagcgcta cgtggccgaa gagggcaccc tcacctccga cctggcggtg     360
ggcgcggccg agcgggcact gaagtccgcc cgcctgacac cggacgagat cgacgcggtc     420
atcgtggcca ccaccactcc ggaccggccc tgccggcga ccgcgccgac ggtggcggcc      480
cggctgggca ccggcccggt cccggcgttc gacgtgtccg cggtgtgctc cggcttcctc     540
tacggactcg ccacggggtc cggtctgatc gcgtccggag cggcggaacg ggtcctggtc     600
atcggtgcgg agaccttctc ccgcatcctc aacccgcagg accgctccac ctcggtgatc     660
ttcggtgacg gcgccggcgc cgtcgtgctg cgcgccggcg agccggggga gaccggtgcc     720
ctcggcccgc tgcggctggg cagcgacggc accggcgtgg acctgatcac cgtgccggcc     780 ggcgaccgc cgcggccggg cgcggcggca ccggacgatc tcgccgaccg ctacttcacc     840
atggagggca agcgggtctt ctggctcgcc gtccagcgca tgggcgagtg cgcggagagc     900
gtgctcgacc gggcgggctg gcgggtggcg gacgtggact ggctggtcag ccaccaggcc     960
aaccaccgca tcaccgcccg gctcgccgac gagatcggga tcccccgcga gcgcagcgtc    1020
agcaacatcg ccgaggtggg caacaccgcc gccgcctcca tcccctcgc gctcgaccac    1080 gcgcacgccc gggccacccct ccggcccggc gaccgggtgc tcctcaccgc cttcggcgga    1140
ggcctcacct ggggtgccgc cgccctgacc tggcccgccg tcgatccggt ctgagggcgg    1200
ccggccgggc ccggccgaag cgcgcgcaga cgaccgatga accaaggacg accatgactc    1260
ctcggaaact gatcaccgac tacatcgccg acgcctggat gggcggcgac gccgaaggcc    1320
tggagccgga caccccatc gcggagctga acatcatcga ctccgccgcc atcttcgacc    1380

<210> SEQ ID NO 3
<211> LENGTH: 446
<212> TYPE: PRT
<213> ORGANISM: Streptomyces coelicolor

<400> SEQUENCE: 3

Met Thr Pro Asp Pro Leu Ala Pro Leu Asp Leu Ala Phe Trp Asn Ile
1               5                   10                  15

Glu Ser Ala Glu His Pro Met His Leu Gly Ala Leu Gly Val Phe Glu
                20                  25                  30

Ala Asp Ser Pro Thr Ala Gly Ala Leu Ala Ala Asp Leu Leu Ala Ala
            35                  40                  45

Arg Ala Pro Ala Val Pro Gly Leu Arg Met Arg Ile Arg Asp Thr Trp
        50                  55                  60

Gln Pro Pro Met Ala Leu Arg Arg Pro Phe Ala Phe Gly Gly Ala Thr
65                  70                  75                  80

Arg Glu Pro Asp Pro Arg Phe Asp Pro Leu Asp His Val Arg Leu His
                85                  90                  95
```

Ala Pro Ala Thr Asp Phe His Ala Arg Ala Gly Arg Leu Met Glu Arg
            100                 105                 110

Pro Leu Glu Arg Gly Arg Pro Trp Glu Ala His Val Leu Pro Gly
        115                 120                 125

Ala Asp Gly Gly Ser Phe Ala Val Leu Phe Lys Phe His His Ala Leu
130                 135                 140

Ala Asp Gly Leu Arg Ala Leu Thr Leu Ala Ala Gly Val Leu Asp Pro
145                 150                 155                 160

Met Asp Leu Pro Ala Pro Arg Pro Arg Pro Glu Gln Pro Pro Arg Gly
                165                 170                 175

Leu Leu Pro Asp Val Arg Ala Leu Pro Asp Arg Leu Arg Gly Ala Leu
            180                 185                 190

Ser Asp Ala Gly Arg Ala Leu Asp Ile Gly Ala Ala Ala Leu Ser
        195                 200                 205

Thr Leu Asp Val Arg Ser Ser Pro Ala Leu Thr Ala Ala Ser Ser Gly
210                 215                 220

Thr Arg Arg Thr Ala Gly Val Ser Val Asp Leu Asp Val His His
225                 230                 235                 240

Val Arg Lys Thr Thr Gly Gly Thr Val Asn Asp Val Leu Ile Ala Val
                245                 250                 255

Val Ala Gly Ala Leu Arg Arg Trp Leu Asp Glu Arg Gly Asp Gly Ser
            260                 265                 270

Glu Gly Val Ala Pro Arg Ala Leu Ile Pro Val Ser Arg Arg Pro
        275                 280                 285

Arg Ser Ala His Pro Gln Gly Asn Arg Leu Ser Gly Tyr Leu Met Arg
290                 295                 300

Leu Pro Val Gly Asp Pro Asp Pro Leu Ala Arg Leu Gly Thr Val Arg
305                 310                 315                 320

Ala Ala Met Asp Arg Asn Lys Asp Ala Gly Pro Gly Arg Gly Ala Gly
                325                 330                 335

Ala Val Ala Leu Leu Ala Asp His Val Pro Ala Leu Gly His Arg Leu
            340                 345                 350

Gly Gly Pro Leu Val Ser Gly Ala Ala Arg Leu Trp Phe Asp Leu Leu
        355                 360                 365

Val Thr Ser Val Pro Leu Pro Ser Leu Gly Leu Arg Leu Gly Gly His
370                 375                 380

Pro Leu Thr Glu Val Tyr Pro Leu Ala Pro Leu Ala Arg Gly His Ser
385                 390                 395                 400

Leu Ala Val Ala Val Ser Thr Tyr Arg Gly Arg Val His Tyr Gly Leu
                405                 410                 415

Leu Ala Asp Ala Lys Ala Val Pro Asp Leu Asp Arg Leu Ala Val Ala
            420                 425                 430

Val Ala Glu Glu Val Glu Thr Leu Leu Thr Ala Cys Arg Pro
        435                 440                 445

<210> SEQ ID NO 4
<211> LENGTH: 335
<212> TYPE: PRT
<213> ORGANISM: Streptomyces coelicolor

<400> SEQUENCE: 4

Met Thr Arg Ala Ser Val Leu Thr Gly Leu Gly Ser Cys Leu Pro Ser
1               5                   10                  15

Arg Cys Val Thr Asn Ala Glu Leu Glu Arg Thr Met Asp Thr Ser Asp
            20                  25                  30

```
Glu Trp Ile Arg Ala Arg Thr Gly Ile Ala Gln Arg Tyr Val Ala Glu
 35                  40                  45
Glu Gly Thr Leu Thr Ser Asp Leu Ala Val Gly Ala Ala Glu Arg Ala
 50                  55                  60
Leu Lys Ser Ala Arg Leu Thr Pro Asp Glu Ile Asp Ala Val Ile Val
 65                  70                  75                  80
Ala Thr Thr Thr Pro Asp Arg Pro Cys Pro Ala Thr Ala Pro Thr Val
                 85                  90                  95
Ala Ala Arg Leu Gly Thr Gly Pro Val Pro Ala Phe Asp Val Ser Ala
                100                 105                 110
Val Cys Ser Gly Phe Leu Tyr Gly Leu Ala Thr Gly Ser Gly Leu Ile
            115                 120                 125
Ala Ser Gly Ala Ala Glu Arg Val Leu Val Ile Gly Ala Glu Thr Phe
        130                 135                 140
Ser Arg Ile Leu Asn Pro Gln Asp Arg Ser Thr Ser Val Ile Phe Gly
145                 150                 155                 160
Asp Gly Ala Gly Ala Val Val Leu Arg Ala Gly Glu Pro Gly Glu Thr
                165                 170                 175
Gly Ala Leu Gly Pro Leu Arg Leu Gly Ser Asp Gly Thr Gly Val Asp
            180                 185                 190
Leu Ile Thr Val Pro Ala Gly Gly Pro Pro Arg Pro Gly Ala Ala Ala
        195                 200                 205
Pro Asp Asp Leu Ala Asp Arg Tyr Phe Thr Met Glu Gly Lys Arg Val
210                 215                 220
Phe Trp Leu Ala Val Gln Arg Met Gly Glu Cys Ala Glu Ser Val Leu
225                 230                 235                 240
Asp Arg Ala Gly Trp Arg Val Ala Asp Val Asp Trp Leu Val Ser His
                245                 250                 255
Gln Ala Asn His Arg Ile Thr Ala Arg Leu Ala Asp Glu Ile Gly Ile
            260                 265                 270
Pro Arg Glu Arg Ser Val Ser Asn Ile Ala Glu Val Gly Asn Thr Ala
        275                 280                 285
Ala Ala Ser Ile Pro Leu Ala Leu Asp His Ala His Ala Arg Gly Thr
        290                 295                 300
Leu Arg Pro Gly Asp Arg Val Leu Leu Thr Ala Phe Gly Gly Gly Leu
305                 310                 315                 320
Thr Trp Gly Ala Ala Ala Leu Thr Trp Pro Ala Val Asp Pro Val
                325                 330                 335

<210> SEQ ID NO 5
<211> LENGTH: 18
<212> TYPE: DNA
<213> ORGANISM: Artificial
<220> FEATURE:
<223> OTHER INFORMATION: Forward primer

<400> SEQUENCE: 5
ggtggagcat gtggttta                                                  18

<210> SEQ ID NO 6
<211> LENGTH: 18
<212> TYPE: DNA
<213> ORGANISM: Artificial
<220> FEATURE:
<223> OTHER INFORMATION: Reverse primer

<400> SEQUENCE: 6
ccattgtagc acgtgtgt                                                  18
```

<210> SEQ ID NO 7
<211> LENGTH: 28
<212> TYPE: DNA
<213> ORGANISM: Artificial
<220> FEATURE:
<223> OTHER INFORMATION: Forward primer

<400> SEQUENCE: 7
atttctagaa aaccgtccat cacgcgag                              28

<210> SEQ ID NO 8
<211> LENGTH: 35
<212> TYPE: DNA
<213> ORGANISM: Artificial
<220> FEATURE:
<223> OTHER INFORMATION: Reverse primer

<400> SEQUENCE: 8
attaagctta ctagtatggt cgtccttggt tcatc                       35

<210> SEQ ID NO 9
<211> LENGTH: 35
<212> TYPE: DNA
<213> ORGANISM: Artificial
<220> FEATURE:
<223> OTHER INFORMATION: Forward primer

<400> SEQUENCE: 9
atttctagaa ctagtgatcg tacttgaccg taatc                       35

<210> SEQ ID NO 10
<211> LENGTH: 36
<212> TYPE: DNA
<213> ORGANISM: Artificial
<220> FEATURE:
<223> OTHER INFORMATION: Reverse primer

<400> SEQUENCE: 10
attaagcttg ctagccgaac agcggatttt attcag                      36

<210> SEQ ID NO 11
<211> LENGTH: 24
<212> TYPE: DNA
<213> ORGANISM: Artificial
<220> FEATURE:
<223> OTHER INFORMATION: Forward primer, wherein S is C or G; Y is C or
      T; B is C, G or T and N is A, T, C or G.

<400> SEQUENCE: 11
tsgcstgctt gcttcgaygc satc                                   24

<210> SEQ ID NO 12
<211> LENGTH: 20
<212> TYPE: DNA
<213> ORGANISM: Artificial
<220> FEATURE:
<223> OTHER INFORMATION: Reverse primer, wherein S is C or G; Y is C or
      T; B is C, G or T and N is A, T, C or G.
<220> FEATURE:
<221> NAME/KEY: misc_feature
<222> LOCATION: (6)..(6)
<223> OTHER INFORMATION: n is a, c, g, or t

<400> SEQUENCE: 12
tggaanccgc cgaabccgct                                        20